US009528987B2

(12) United States Patent
Yager et al.

(10) Patent No.: US 9,528,987 B2
(45) Date of Patent: Dec. 27, 2016

(54) REAGENT PATTERNING IN CAPILLARITY-BASED ANALYZERS AND ASSOCIATED SYSTEMS AND METHODS

(75) Inventors: Paul Yager, Seattle, WA (US); Barry R. Lutz, Seattle, WA (US); Elain S. Fu, Corvallis, OR (US); Gina Fridley, Seattle, WA (US); Huy Quang Le, Redmond, WA (US); Peter C. Kauffman, Bainbridge Island, WA (US)

(73) Assignee: University of Washington, Seattle, WA (US)

( * ) Notice: Subject to any disclaimer, the term of this patent is extended or adjusted under 35 U.S.C. 154(b) by 301 days.

(21) Appl. No.: 14/129,078

(22) PCT Filed: Jun. 25, 2012

(86) PCT No.: PCT/US2012/044060
§ 371 (c)(1),
(2), (4) Date: Mar. 24, 2014

(87) PCT Pub. No.: WO2012/178187
PCT Pub. Date: Dec. 27, 2012

(65) Prior Publication Data
US 2014/0227707 A1 Aug. 14, 2014

Related U.S. Application Data

(60) Provisional application No. 61/501,055, filed on Jun. 24, 2011, provisional application No. 61/609,667, filed on Mar. 12, 2012.

(51) Int. Cl.
| | | |
|---|---|---|
| *G01N 33/543* | (2006.01) | |
| *B01L 3/00* | (2006.01) | |
| *C12Q 1/68* | (2006.01) | |
| *G01N 33/569* | (2006.01) | |

(52) U.S. Cl.
CPC ....... *G01N 33/54386* (2013.01); *B01L 3/5023* (2013.01); *B01L 3/50273* (2013.01); *B01L 3/502707* (2013.01); *B01L 3/502738* (2013.01); *B01L 3/502746* (2013.01); *C12Q 1/6844* (2013.01); *G01N 33/56905* (2013.01); *B01L 2200/0621* (2013.01); *B01L 2300/069* (2013.01); *B01L 2300/0816* (2013.01); *B01L 2300/0861* (2013.01); *B01L 2400/0406* (2013.01); *B01L 2400/0677* (2013.01); *B01L 2400/086* (2013.01); *B01L 2400/088* (2013.01)

(58) Field of Classification Search
None
See application file for complete search history.

(56) References Cited

U.S. PATENT DOCUMENTS

| | | |
|---|---|---|
| 3,667,607 A | 6/1972 | Brandt |
| 4,235,601 A | 11/1980 | Deutsch et al. |
| 4,632,901 A | 12/1986 | Valkirs et al. |
| 4,647,430 A | 3/1987 | Zweig |
| 4,727,019 A | 2/1988 | Valkirs et al. |
| 4,810,470 A | 3/1989 | Burkhardt et al. |
| 4,861,711 A | 8/1989 | Friesen et al. |
| 4,960,691 A | 10/1990 | Gordon et al. |
| 4,987,085 A | 1/1991 | Allen et al. |
| 5,079,142 A | 1/1992 | Coleman et al. |
| 5,110,724 A | 5/1992 | Hewett |
| 5,135,872 A | 8/1992 | Ingalz et al. |
| 5,185,242 A | 2/1993 | Keating et al. |
| 5,198,193 A | 3/1993 | Bunce et al. |
| 5,354,538 A * | 10/1994 | Bunce .................... B01L 3/502 422/520 |
| 5,369,007 A | 11/1994 | Kidwell |
| 5,516,488 A | 5/1996 | Bunce et al. |
| 5,540,888 A | 7/1996 | Bunce et al. |
| 5,565,318 A | 10/1996 | DiFrancesco et al. |
| 5,593,824 A | 1/1997 | Treml et al. |
| 5,618,494 A | 4/1997 | Bunce et al. |
| 5,705,397 A | 1/1998 | Bunce et al. |

(Continued)

FOREIGN PATENT DOCUMENTS

| | | | | |
|---|---|---|---|---|
| AU | WO 2010003188 A1 * | 1/2010 | ........ | B01L 3/502707 |
| CN | 1500555 A | 6/2004 | | |

(Continued)

OTHER PUBLICATIONS

Fu et al. (Chemical signal amplification in two-dimensional paper networks, Sensors and Actuators B: Chemical vol. 149, Issue 1, Aug. 6, 2010, pp. 325-328, Jun. 18, 2010).*
Fu et al. (hereinafter "Fu2"; Controlled reagent transport in disposable 2D paper networks, Lab Chip. Author manuscript; available in PMC Dec. 1, 2011. Published in final edited form as: Lab Chip. Apr. 7, 2010; 10(7): 918-920. Published online Jan. 15, 2010).*
Fu et al. (hereinafter "Fu3"; Transport in two-dimensional paper networks, Microfluid Nanofluidics. Author manuscript; available in PMC Jan. 1, 2012. Published in final edited form as: Microfluid Nanofluidics. Jan. 2011; 10(1): 29-35).*
Fu et al. (hereinafter "Fu5"; Microfluidics 2.0, Presentation, available at http://depts.washington.edu/cpac/Activities/Meetings/Fall/2010/documents/YagerCPACtalkNov2010.pdf, Nov. 11, 2010).*

(Continued)

*Primary Examiner* — Aaron Priest
(74) *Attorney, Agent, or Firm* — Perkins Coie LLP

(57) ABSTRACT

The present technology describes various embodiments of devices for processing, analyzing, detecting, measuring, and separating fluids. The devices can be used to perform these processes on a microfluidic scale, and with control over fluid and reagent transport. In one embodiment, for example, a device for performing chemical processes can include a porous wick comprising a pathway defined by an input end, an output end, and a length between the input end and the output end. The pathway is configured to wick fluid from the input end to the output end by capillary action. The device can further include a reagent placed on the pathway. The reagent can be placed in a pattern configured to control a spatial or temporal distribution of the reagent along the pathway upon wetting of the pathway.

14 Claims, 14 Drawing Sheets

(56) References Cited

U.S. PATENT DOCUMENTS

| | | |
|---|---|---|
| 5,716,852 A | 2/1998 | Brody et al. |
| 5,736,188 A | 4/1998 | Alcock et al. |
| 5,763,157 A | 6/1998 | Treml et al. |
| 5,801,155 A | 9/1998 | Kutyavin et al. |
| 5,853,670 A | 12/1998 | Bunce |
| 5,916,521 A | 6/1999 | Bunce et al. |
| 5,932,100 A | 8/1999 | Forster et al. |
| 6,007,999 A | 12/1999 | Clark |
| 6,017,767 A | 1/2000 | Chandler |
| 6,084,102 A | 7/2000 | Kutyavin et al. |
| 6,127,121 A | 10/2000 | Afonina et al. |
| 6,146,589 A | 11/2000 | Chandler |
| 6,303,389 B1 | 10/2001 | Levin et al. |
| 6,312,894 B1 | 11/2001 | Hedgpeth et al. |
| 6,485,906 B2 | 11/2002 | Meyer, Jr. et al. |
| 6,486,308 B2 | 11/2002 | Kutyavin et al. |
| 6,492,346 B2 | 12/2002 | Hedgpeth et al. |
| 6,663,833 B1 | 12/2003 | Stave et al. |
| 6,683,173 B2 | 1/2004 | Dempcy et al. |
| 6,742,661 B1 | 6/2004 | Weigl et al. |
| 6,849,414 B2 | 2/2005 | Guan et al. |
| 6,884,584 B2 | 4/2005 | Hedgpeth et al. |
| 6,949,367 B1 | 9/2005 | Dempcy et al. |
| 6,989,128 B2 | 1/2006 | Alajoki et al. |
| 7,045,610 B2 | 5/2006 | Dempcy et al. |
| 7,112,444 B2 | 9/2006 | Beebe et al. |
| 7,141,429 B2 | 11/2006 | Kamholz et al. |
| 7,179,639 B2 | 2/2007 | Pottathil et al. |
| 7,189,522 B2 | 3/2007 | Esfandiari |
| 7,300,802 B2 | 11/2007 | Paek et al. |
| 7,314,060 B2 | 1/2008 | Chen et al. |
| 7,368,549 B2 | 5/2008 | Dempcy et al. |
| 7,682,817 B2 | 3/2010 | Cohen et al. |
| 7,715,989 B2 | 5/2010 | Dempcy et al. |
| 7,794,945 B2 | 9/2010 | Hedgpeth et al. |
| 8,685,749 B2 | 4/2014 | Shoemaker et al. |
| 8,900,850 B2 | 12/2014 | Gavalchin et al. |
| 9,101,927 B2 | 8/2015 | Alajem et al. |
| 9,207,236 B2 | 12/2015 | Cary et al. |
| 2002/0179445 A1 | 12/2002 | Alajoki et al. |
| 2004/0152207 A1 | 8/2004 | Nelson et al. |
| 2004/0166504 A1 | 8/2004 | Rossier et al. |
| 2006/0160078 A1* | 7/2006 | Cardy .................. B01L 3/5023 435/6.11 |
| 2006/0246600 A1* | 11/2006 | Yang ................ G01N 33/54366 436/514 |
| 2007/0020768 A1 | 1/2007 | Rundstrom et al. |
| 2008/0145835 A1 | 6/2008 | Alajem et al. |
| 2008/0220520 A1* | 9/2008 | Palecek .................... A01N 1/02 435/374 |
| 2008/0248098 A1* | 10/2008 | Jin ....................... A61K 9/1623 424/450 |
| 2009/0004732 A1 | 1/2009 | LaBarre et al. |
| 2009/0011472 A1 | 1/2009 | Nelson et al. |
| 2009/0142229 A1* | 6/2009 | MacDonald ......... G01N 33/491 422/68.1 |
| 2009/0197296 A1 | 8/2009 | Martin et al. |
| 2009/0298191 A1 | 12/2009 | Whitesides et al. |
| 2010/0143905 A1 | 6/2010 | Lane et al. |
| 2010/0210037 A1* | 8/2010 | Brown .............. B01L 3/502738 436/518 |
| 2010/0210038 A1 | 8/2010 | Blatt et al. |
| 2010/0233708 A1 | 9/2010 | Mehra et al. |
| 2011/0081641 A1 | 4/2011 | Gould et al. |
| 2011/0165559 A1 | 7/2011 | Lane et al. |
| 2011/0189792 A1 | 8/2011 | Reinhartz et al. |
| 2012/0028498 A1 | 2/2012 | Na et al. |
| 2012/0288961 A1 | 11/2012 | Yager et al. |
| 2013/0017559 A1* | 1/2013 | Babu ..................... B01L 3/5023 435/7.9 |
| 2013/0164193 A1 | 6/2013 | Semenov et al. |
| 2015/0361487 A1 | 12/2015 | Bishop et al. |

FOREIGN PATENT DOCUMENTS

| | | | |
|---|---|---|---|
| EP | 0151783 A2 | 8/1985 | |
| EP | 0314499 A1 | 5/1989 | |
| EP | 0520756 B1 | 4/1995 | |
| GB | 2261284 A2 | 5/1993 | |
| GB | 2410086 A | 7/2005 | |
| WO | 9734148 A1 | 9/1997 | |
| WO | 0125789 A1 | 4/2001 | |
| WO | 0136974 A1 | 5/2001 | |
| WO | 2008049083 A2 | 4/2008 | |
| WO | 2009137059 A1 | 11/2009 | |
| WO | 2010102294 A1 | 9/2010 | |
| WO | 2011087813 A2 | 7/2011 | |
| WO | WO 2011087813 A2 * | 7/2011 | ............ B01L 3/5023 |
| WO | 2011115975 A2 | 9/2011 | |
| WO | 2012178187 A1 | 12/2012 | |
| WO | 2014116756 A1 | 7/2014 | |

OTHER PUBLICATIONS

Osborn et al. (Microfluidics without pumps: reinventing the T-sensor and H-filter in paper networks, Lab Chip. Oct. 21, 2010;10(20):2659-65. doi: 10.1039/c004821f. Epub Aug. 3, 2010).*

Fu et al. (Two-dimensional paper network format that enables simple multistep assays for use in low-resource settings in the context of malaria antigen detection, Anal Chem. May 15, 2012;84(10):4574-9. doi: 10.1021/ac300689s. Epub Apr. 26, 2012).*

Fu et al. (Two-dimensional paper network format for amplified lateral flow assays, 5th International Conference on Miniaturized Systems for Chemistry and Life Sciences 2011, MicroTAS 2011. (vol. 3, pp. 1891-1893)).*

Foley et al. (Experimental and model investigation of the time-dependent 2-dimensional distribution of binding in a herringbone microchannel, Lab Chip. Apr. 2008;8(4):557-64. doi: 10.1039/b713644g. Epub Feb. 21, 2008).*

Fenton et al. (Multiplex Lateral-Flow Test Strips Fabricated by Two-Dimensional Shaping, ACS Appl Mater Interfaces. Jan. 2009;1(1):124-9).*

Rao et al. (Developing rapid, point-of-care, multiplex detection for use in lateral flow devices, Proceedings of SPIE—The International Society for Optical Engineering 6007, Oct. 2005).*

Agida et al. (Stimuli-Responsive Polymer Brushes for Flow Control through Nanopores, J Funct Biomater. Jun. 2012; 3(2): 239-256. Published online Mar. 26, 2012).*

Lokuge et al. (Temperature-controlled flow switching in nanocapillary array membranes mediated by poly(N-isopropylacrylamide) polymer brushes grafted by atom transfer radical polymerization, Langmuir. Jan. 2, 2007;23(1):305-11).*

Sun et al. (Reversible switching between superhydrophilicity and superhydrophobicity, Angew Chem Int Ed Engl. Jan. 3, 2004;43(3):357-60).*

Li et al. (Paper-based microfluidic devices by plasma treatment, Anal Chem. Dec. 1, 2008;80(23):9131-4).*

Abe, K. et al. (Sep. 2010) "Inkjet-printed paperfluidic immuno-chemical sensing device," Analytical and Bioanalytical Chemistry, 398(2):885-893.

Aiello, AE et al. (Jun. 2006) "Meticillin-resistant *Staphylococcus aureus* among US prisoners and military personnel: review and recommendations for future studies," Lancet Infectious Diseases, 6(6):335-341.

Anchordoquy, TJ and Molina, MC (Jan. 2008) "Preservation of DNA," Cell Preservation Technology, 5(4):180-188.

Apilux, A. et al. (Mar. 2010) "Lab-on-paper with dual electrochemical/colorimetric detection for simultaneous determination of gold and iron," Analytical Chemistry, 82(5):1727-1732.

Arai, H. et al. (Feb. 1999) "Evaluation of a rapid immunochromatographic test for detection of antibodies to human immunodeficiency virus," Journal of Clinical Microbiology, 37(2):367-370.

Bauer, KA et al. (Nov. 2010) "An Antimicrobial Stewardship Program's Impact with Rapid Polymerase Chain Reaction Methicil-

(56) References Cited

OTHER PUBLICATIONS lin-Resistant *Staphylococcus aureus/S. aureus* Blood Culture Test in Patients with *S. aureus* Bacteremia," Clinical Infectious Diseases, 51(9):1074-1080.

Baum, SE et al. (Feb. 2003) "Methicillin-resistant *Staphylococcus aureus* in an adult military beneficiary population lacking risk factors: Susceptibility to orally available agents," Military Medicine, 168(2):126-130.

Belousov, Y. et al. (Mar. 2004) "Single nucleotide polymorphism genotyping by two colour melting curve analysis using the MGB Eclipse Probe System in challenging sequence environment," Human Genomics, 1(3):209-217.

Blanc, DS et al. (Feb. 2011) "High proportion of wrongly identified methicillin-resistant *Staphylococcus aureus* carriers by use of a rapid commercial PCR assay due to presence of staphylococcal cassette chromosome element lacking the mecA gene," Journal of Clinical Microbiology, 49(2):722-724.

Boyd, S. and Yamazaki, H. (May 1996) "Long-term preservation of antibody activity and binding to polyester cloth by dessication," Biotechnology Techniques, 10(5):367-370.

Brenwald, NP et al. (Mar. 2010) "Feasibility study of a real-time PCR test for methicillin-resistant *Staphylococcus aureus* in a point of care setting," Journal of Hospital Infection, 74(3):245-249.

Bruzewicz, DA et al. (May 2008) "Low-cost printing of poly(dimethylsiloxane) barriers to define microchannels in paper," Analytical Chemistry, 80(9):3387-3392.

Buitink, J. et al. (Aug. 2000) "High Critical Temperature above $T_g$ May Contribute to the Stability of Biological Systems," Biophysical Journal, 79(2):1119-1128.

Campbell, KM et al. (Sep. 2004) "Risk factors for community-associated methicillin-resistant *Staphylococcus aureus* infections in an outbreak of disease among military trainees in San Diego, California, in 2002," Journal of Clinical Microbiology, 42(9):4050-4053.

Carpenter, JF et al. (Jan. 1987) "Stabilization of Phosphofructokinase with Sugars during Freeze-Drying—Characterization of Enhanced Protection in the Presence of Divalent-Cations," Biochimica et Biophysica Acta, 923(1):109-115.

Carrilho, E. et al. (Aug. 2009) "Understanding Wax Printing: A Simple Micropatterning Process for Paper-Based Microfluidics," Analytical Chemistry, 81(16):7091-7095.

Carter, DJ and Cary, RB (epub May 2007) "Lateral flow microarrays: a novel platform for rapid nucleic acid detection based on miniaturized lateral flow chromatography," Nucleic Acids Research, 35(10):e74, 11 pp.

Center for Disease Control (Aug. 2009) "Interim guidance for detection of novel influenza A virus using rapid influenza testing," available at: http://www.cdc.gov/h1n1flu/guidance/rapid_testing.htm.

Chembio Diagnostic Systems, Inc. (Apr. 2009; retrieved Jan. 2015) "Dual Path Platform (DPP*) Technology," available online at: <http://www.chembio.com/newtechnologies.html>.

Chickering, HT and Park, JH (Mar. 1919) "*Staphylococcus aureus* pneumonia," Journal of the American Medical Association, 72(9):617-626.

Chin, CD et al. (Jan. 2007) "Lab-on-a-chip devices for global health: past studies and future opportunities," Lab on a Chip, 7(1):41-57.

Cho, IH et al. (Jan. 2010) "Immunogold-silver staining-on-a-chip biosensor based on cross-flow chromatography," Journal of Chromatography B: Analytical Technologies in the Biomedical and Life Sciences, 878(2):271-277.

Cho, JH et al. (Feb. 2006) "Plastic ELISA-on-a-chip based on sequential cross-flow chromatography," Analytical Chemistry, 78(3):793-800.

Chun, P. (2009; retrieved Mar. 2016) "Colloidal Gold and Other Labels for Lateral Flow Immunoassays," in *Lateral Flow Immunoassay*, eds. R. Wong and H. Tse, Humana Press: New York, pp. 75-94.

Co, EM et al. (Jan. 2011) "Prevalence of Methicillin-Resistant *Staphylococcus aureus* in a Combat Support Hospital in Iraq," Military Medicine, 176(1):89-93.

Corstjens, P. et al. (Jan. 2003) "Lateral-flow and up-converting phosphor reporters to detect single-stranded nucleic acids in a sandwich-hybridization assay," Analytical Biochemistry, 312(2):191-200.

Corstjens, P., et al. (Oct. 2001) "Use of up-converting phosphor reporters in lateral-flow assays to detect specific nucleic acid sequences: A rapid, sensitive DNA test to identify human papillomavirus type 16 infection," Clinical Chemistry, 47(10):1885-1893.

Cretich, M. et al. (Feb. 2010) "Coating of nitrocellulose for colorimetric DNA microarrays," Analytical Biochemistry, 397(1):84-88.

Crowe, LM et al. (Oct. 1996) "Is trehalose special for preserving dry biomaterials?" Biophysical Journal, 71(4):2087-2093.

Crum, NF et al. (Nov. 2006) "Fifteen-year study of the changing epidemiology of methicillin-resistant *Staphylococcus aureus*," American Journal of Medicine, 119(11):943-951.

Desai, D. et al. (Jan. 2011) "Tackling HIV through robust diagnostics in the developing world: current status and future opportunities," Lab on a Chip, 11(2):194-211.

Diagnostics for All (2010; retrieved Mar. 2016) "Diagnostics for All: Patterned-paper microfluidics as a low-cost platform for advanced point-of-care diagnostics in low-resource settings," available at http://www.dfa.org/index.html, 1 page.

Drexler, JF et al. (Oct. 2009) "Poor Clinical Sensitivity of Rapid Antigen Test for Influenza A Pandemic (H1N1) 2009 Virus," Emerging Infectious Diseases, 15(10):1662-1664.

Dungchai, W. et al. (Aug. 2010) "Use of multiple colorimetric indicators for paper-based microfluidic devices," Analytica Chimica Acta, 674(2):227-233.

Eddington, DT and Beebe, DJ (Feb. 2004) "Flow control with hydrogels," Advanced Drug Delivery Reviews, 56(2):199-210.

Edwards, KA and Baeumner, AJ (Nov. 2006) "Optimization of DNA-tagged dye-encapsulating liposomes for lateral-flow assays based on sandwich hybridization," Analytical and Bioanalytical Chemistry, 386(5):1335-1343.

Eijkel, Jan C.T. (Nov. 2006) "Young 4ever—the use of capillarity for passive flow handling in lab on a chip devices," Lab on a Chip, 6(11):1405-1408.

Elias, ME and Elias, AM (Dec. 1999) "Trehalose + water fragile system: properties and glass transition," Journal of Molecular Liquids, 83(1-3):303-310.

Ellis, MW et al. (Oct. 2004) "Natural history of community-acquired methicillin-resistant *Staphylococcus aureus* colonization and infection in soldiers," Clinical Infectious Diseases, 39(7):971-979.

Engler, K.H. et al. (Jan. 2002) "Immunochromatographic strip test for rapid detection of diphtheria toxin: Description and multicenter evaluation in areas of low and high prevalence of diphtheria," Journal of Clinical Microbiology, 40(1):80-83.

Englund, JA (2001; retrieved Mar. 2016) "Diagnosis and Epidemiology of Community-Acquired Respiratory Virus Infections in the Immunocompromised Host," Biology of Blood and Marrow Transplantation, 7(Suppl):2S-4S.

Fairchok, MP et al. (Sep. 2010) "Epidemiology of viral respiratory tract infections in a prospective cohort of infants and toddlers attending daycare," Journal of Clinical Virology, 49(1):16-20.

Farzamfar, B. et al. (2007; retrieved Mar. 2016) "The effect of different stabilizers on stability of horseradish peroxidase-bovine serum albumin-aflatoxin B1, a conjugated tracer for detection of aflatoxin B1 in immunoassay-based methods," Iranian Journal of Pharmaceutical Research, 6(3):179-184.

Faulstich, K. et al. (2009; retrieved Mar. 2016) "Handheld and Portable Reader Devices for Lateral Flow Immunoassays," in *Lateral Flow Immunoassay*, eds. R. Wong and H. Tse, Humana Press: New York, pp. 157-183.

Fenton, EM et al. (Jan. 2009) "Multiplex lateral-flow test strips fabricated by two-dimensional shaping," Applied Materials and Interfaces, 1(1):124-129.

(56) References Cited

OTHER PUBLICATIONS

Foley, JO et al. (Apr. 2008) "Experimental and model investigation of the time-dependent 2-dimensional distribution of binding in a herringbone microchannel," Lab on a Chip, 8(4):557-564.

Foley, JO et al. (May 2007) "Concentration gradient immunoassay. 2. Computational modeling for analysis and optimization," Analytical Chemistry, 79(10):3549-3553.

Fornera, S. et al. (Aug. 2011) "Immobilization of Peroxidase on SiO(2) Surfaces with the Help of a Dendronized Polymer and the Avidin-Biotin System," Macromolecular Bioscience, 11(8):1052-1067.

Fu, E. et al. (Aug. 2010) "Chemical signal amplification in two-dimensional paper networks," Sensors and Actuators B-Chemical, 149(1):325-328.

Fu, E. et al. (Jan. 2011) "Transport in two-dimensional paper networks," Microfluidics and Nanofluidics, 10(1):29-35.

Fu, E. et al. (May 2009) "Modeling of a Competitive Microfluidic Heterogeneous Immunoassay: Sensitivity of the Assay Response to Varying System Parameters," Analytical Chemistry, 81(9):3407-3413.

Fu, E. et al. (May 2012) "A two-dimensional paper network format that enables simple multi-step assays for use in low-resource settings," Analytical Chemistry, 84(10):4574-4579.

Fu, E. et al. (Oct. 2011) "Enhanced Sensitivity of Lateral Flow Tests Using a Two-Dimensional Paper Network Format," Analytical Chemistry, 83(20):7941-7946.

Fu, Elain et al. (epub Jan. 2010) "Controlled reagent transport in disposable 2D paper networks," Lab on a Chip, 10(7):918-920.

GE Healthcare Life Sciences (Apr. 2009; retrieved Jan. 2015) "Whatman Filters & Sample Collection," available online at: http://www.whatman.com/References/FINAL%20FTAProtect&StorageDNADataSheet%204-30-09LR.pdf.

Gervais, L. and Delamarche, E. (Dec. 2009) "Toward one-step point-of-care immunodiagnostics using capillary-driven microfluidics and PDMS substrates," Lab on a Chip, 9(23):3330-3337.

Gibson, TD et al. (Jul. 1993) "Preservation of Shelf-Life of Enzyme-Based Analytical Systems Using a Combination of Sugars, Sugar Alcohols and Cationic Polymers of Zinc Ions," Analytical Chimica Acta, 279(1):185-192.

Govindarajan, A. et al. (Jan. 2011) "Microfluidic origami for point-of-care extraction of nucleic acids from viscous samples," In Proceedings of the IEEE 24$^{th}$ International Conference on Micro Electrical Mechanical Systems (MEMS '11), Cancun, Mexico, pp. 932-935.

Horton, JK et al. (Jun. 1991) "A novel, rapid, single-step immunochromatographic procedure for the detection of mouse immunoglobulin," Journal of Immunological Methods, 140(1):131-134.

Huang, XZ et al. (Jul. 2011) "Methicillin-resistant *Staphylococcus aureus* infection in combat support hospitals in three regions of Iraq," Epidemiology and Infection, 139(7):994-997.

Hurt, AC et al. (Jun. 2007) "Performance of six influenza rapid tests in detecting human influenza in clinical specimens," Journal of Clinical Virology, 39(2):132-135.

Hymas, W. et al. (Aug. 2010) "Development of a multiplex real-time RT-PCR assay for detection of influenza A, influenza B, RSV and typing of the 2009-H1N1 influenza virus," Journal of Virological Methods, 167(2):113-118.

International Search Report and Written Opinion dated Jun. 9, 2011 for PCT/US2010/061675 filed Dec. 21, 2010, 18 pages.

International Search Report and Written Opinion dated Nov. 7, 2012 for International Patent Application No. PCT/US2012/044060 filed Jun. 25, 2012.

International Search Report and Written Opinion dated May 14, 2014 for PCT/US2014/012618 filed Jan. 22, 2014, 17 pages.

Izutsu, KI et al. (Jul. 1994) "Physical Stability and Protein Stability of Freeze-Dried Cakes during Storage at Elevated-Temperatures," Pharmaceutical Research, 11(7):995-999.

Jain, R. et al. (Apr. 2011) "Veterans Affairs Initiative to Prevent Methicillin-Resistant *Staphylococcus aureus* Infections," New England Journal of Medicine, 364(15):1419-1430.

Juncker, D. et al. (Dec. 2002) "Autonomous microfluidic capillary system," Analytical Chemistry, 74(24):6139-6144.

Juncker, David (May 2002) "Capillary microfluidic systems for bio/chemistry," Ph.D. Thesis, Université de Neuchâtel Faculté des sciences, Switzerland, 97 pages.

Kallen, AJ et al. (Mar. 2000) "Increase in community-acquired methicillin-resistant *Staphylococcus aureus* at a Naval Medical Center," Infection Control and Hospital Epidemiology, 21(3):223-226.

Kalogianni, DP et al. (May 2011) "Carbon nano-strings as reporters in lateral flow devices for DNA sensing by hybridization," Analytical and Bioanalytical Chemistry, 400(4):1145-1152.

Kauffman, P. et al. (Oct. 2010) "Visualization and measurement of flow in two-dimensional paper networks," Lab on a Chip, 10(19):2614-2617.

Kay, M. et al. (Apr. 2011) "Shedding of Pandemic (H1N1) 2009 Virus among Health Care Personnel, Seattle, Washington, USA," Emerging Infectious Diseases, 17(4):639-644.

Kenner, J. et al. (Jun. 2003) "Rates of carriage of methicillin-resistant and methicillin-susceptible *Staphylococcus aureus* in an outpatient population," Infection Control and Hospital Epidemiology, 24(6):439-444.

Kettler, H. et al. (2004; retrieved Mar. 2016) "Mapping the landscape of diagnosis for sexually transmitted infections," World Health Organization on behalf of the Special Programme for Research and Training in Tropical Diseases (TDR), 44 pp.

Kifude, CM et al. (Jun. 2008) "Enzyme-linked immunosorbent assay for detection of Plasmodium falciparum histidine-rich protein 2 in blood, plasma, and serum," Clinical and Vaccine Immunology, 15(6):1012-1018.

Klevens, RM et al. (Oct. 2007) "Invasive methicillin-resistant *Staphylococcus aureus* infections in the United States," JAMA-Journal of the American Medical Association, 298(15):1763-1771.

Kline, MC et al. (Apr. 2002) "Polymerase chain reaction amplification of DNA from aged blood stains: Quantitative evaluation of the "suitability for purpose" of four filter papers as archival media," Analytical Chemistry, 74(8):1863-1869.

KO, Jong Soo et al. (Oct. 2003) "Polymer-Based microfluidic device for immunosensing LOC (Lab-on-a-Chip)," 7$^{th}$ International Conference on Miniaturized Chemical and Biochemical Analysts Systems, pp. 295-298.

Kolosova, AY et al. (Feb. 2007) "Investigation of several parameters influencing signal generation in flow-through membrane-based enzyme immunoassay," Analytical and Bioanalytical Chemistry, 387(3):1095-1104.

Kutyavin, IV et al. (Jan. 2000) "3'-minor groove binder-DNA probes increase sequence specificity at PCR extension temperatures," Nucleic Acids Research, 28(2):655-661.

Kutyavin, IV et al. (Nov. 2002) "Reduced aggregation and improved specificity of G-rich oligodeoxyribonucleotides containing pyrazolo[3,4-d]pyrimidine guanine bases," Nucleic Acids Research, 30(22):4952-4959.

Labarre, P. et al. (May 2011) "A Simple, Inexpensive Device for Nucleic Acid Amplification without Electricity—Toward Instrument—Free Molecular Diagnostics in Low-Resource Settings," PLoS One, 6(5):e19738.

Lamar, JE et al. (Feb. 2003) "Sentinel cases of community-acquired methicillin-resistant *Staphylococcus aureus* onboard a naval ship," Military Medicine, 168(2):135-138.

Lei, KF and Butt, YKC (Jan. 2010) "Colorimetric immunoassay chip based on gold nanoparticles and gold enhancement," Microfluidics and Nanofluidics, 8:131-137.

Lei, KF and Wong, KS (epub Sep. 2010) "Automated Colorimetric Immunoassay Microsystem for Clinical Diagnostics," Instrumentation Science and Technology, 38(4):295-304.

Leirião, PR et al. (Jul. 2003) "Horseradish peroxidase immobilized through its carboxylic groups onto a polyacrylonitrile membrane—Comparison of enzyme performances with inorganic beaded supports," Applied Biochemistry and Biotechnology, 110(1):1-10.

(56) References Cited

OTHER PUBLICATIONS

Léonforte, F. et al. (May 2011) "Molecular transport and flow past hard and soft surfaces: computer simulation of model systems," Journal of Physics-Condensed Matter, 23(18):184105, 21 pp.
Li, JJ et al. (May 2008) "Optical scanner for immunoassays with up-converting phosphorescent labels," IEEE Transactions on Biomedical Engineering, 55(5):1560-1571.
Li, X. et al. (Dec. 2008) "Paper-based microfluidic devices by plasma treatment," Analytical Chemistry, 80(23):9131-9134.
Li, X. et al. (Jan. 2010) "Quantitative biomarker assay with microfluidic paper-based analytical devices," Analytical and Bioanalytical Chemistry, 396(1):495-501.
Ligler, FS (Jan. 2009) "Perspective on Optical Biosensors and Integrated Sensor Systems," Analytical Chemistry, 81(2):519-526.
Lin, J-J et al. (2007; retrieved Mar. 2016) "Novel dry-type glucose sensor based on a metal-oxide-semiconductor capacitor structure with horseradish peroxidase plus glucose oxidase catalyzing layer," Japanese Journal of Applied Physics, 46(10A):6871-6874.
Liu, Kk et al. (epub Jul. 2010) "Microfluidic systems for biosensing," Sensor, 10(7):6623-6661.
Lu, Y. et al. (Feb. 2009) "Low cost, portable detection of gold nanoparticle-labeled microfluidic immunoassay with camera cell phone," Electrophoresis, 30(4):579-582.
Lutz, B. et al. (Jul. 2013) "Dissolvable fluidic time delays for programming multi-step assays in instrument-free paper diagnostics," Lab on a Chip, 13(14):2840-2847.
Lutz, BR et al. (Dec. 2011) "Two-dimensional paper networks: programmable fluidic disconnects for multi-step processes in shaped paper," Lab on a Chip, 11(24):4274-4278.
Malhotra-Kumar, S. et al. (Dec. 2010) "Evaluation of molecular assays for rapid detection of methicillin-resistant *Staphylococcus aureus*," Journal of Clinical Microbiology, 48(12):4598-4601.
Mao, X. et al. (Feb. 2009) "Disposable Nucleic Acid Biosensors Based on Gold Nanoparticle Probes and Lateral Flow Strip," Analytical Chemistry, 81(4):1660-1668.
Marner, ES et al. (Apr. 2011) "Diagnostic accuracy of the Cepheid GeneXpert vanA/vanB assay ver. 1.0 to detect the vanA and vanB vancomycin resistance genes in Enterococcus from perianal specimens," Diagnostic Microbiology and Infectious Disease, 69(4):382-389.
Martinez, AW et al. (Dec. 2008) "FLASH: A rapid method for prototyping paper-based microfluidic devices," Lab on a Chip, 8(12):2146-2150.
Martinez, AW et al. (Dec. 2008) "Three-dimensional microfluidic devices fabricated in layered paper and tape," Proceedings of the National Academy of Sciences USA, 105(50):19606-19611.
Martinez, AW et al. (Feb. 2007) "Patterned paper as platform for inexpensive portable bioassays," Angewandte Chemie International Edition, 46(81):1318-1320.
Martinez, AW et al. (May 2008) "Simple Telemedicine for Developing Regions: Camera Phones and Paper-Based Microfluidic Devices for Real-Time Off-Site Diagnosis," Analytical Chemistry, 80(10):3699-3707.
Martinez, AW et al. (Oct. 2010) "Programmable diagnostic devices made from paper and tape," Lab on a Chip, 10(19):2499-2504.
Masson, M. et al. (Sep. 1993) "Chemical Activation of Nitrocellulose Membranes for Peptide Antigen-Antibody Binding-Studies—Direct Substitution of the Nitrate Group with Diaminoalkane," Electrophoresis, 14(9):860-865.
Mazzobre, MF et al. (May 1997) "Protective role of trehalose on thermal stability of lactase in relation to its glass and crystal forming properties and effect of delaying crystallization," LWT—Food Science and Technology, 30(3):324-329.
Mendez, S. et al. (Jan. 2010) "Imbibition in porous membranes of complex shape: quasi-stationary flow in thin rectangular segments," Langmuir, 26(2):1380-1385.
Miller, DP et al. (Aug. 1998) "Stabilization of lactate dehydrogenase following freeze-thawing and vacuum-drying in the presence of trehalose and borate," Pharmaceutical Research, 15(8):1215-1221.

Molinari, NA et al. (Jun. 2007) "The annual impact of seasonal influenza in the US: Measuring disease burden and costs," Vaccine, 25(27):5086-5096.
Monto, AS et al. (Nov. 2000) "Clinical Signs and Symptoms Predicting Influenza Infection," Archives of Internal Medicine, 160(21):3243-3247.
Morrison-Rodriguez, SM et al. (May 2010) "Community-associated methicillin-resistant *Staphylococcus aureus* infections at an Army training installation," Epidemiology and Infection, 138(5):721-729.
Natarajan, P. et al. (Dec. 2000) "Paper-based archiving of mammalian and plant samples for RNA analysis," Biotechniques, 29(6):1328-1333.
Nie, Z. et al. (Nov. 2010) "Integration of paper-based microfluidic devices with commercial electrochemical readers," Lab on a Chip, 10(22):3163-3169.
Nielsen, K. (May 1995) "Stability of Freeze-Dried Horseradish-Peroxidase Conjugated Monoclonal-Antibodies Used in Diagnostic Serology," Journal of Immunoassay, 16(2):183-197.
Niemz, A. et al. (May 2011) "Point-of-care nucleic acid testing for infectious diseases," Trends in Biotechnology, 29(5):240-250.
Noguera, P. et al. (Jan. 2011) "Carbon nanoparticles in lateral flow methods to detect genes encoding virulence factors of Shiga toxin-producing *Escherichia coli*," Analytical and Bioanalytical Chemistry, 399(2):831-838.
Noh, H. and Philips, ST (May 2010) "Metering the capillary-driven flow of fluids in paper-based microfluidic devices," Analytical Chemistry, 82(10):4181-4187.
Noh, H. and Philips, ST (Oct. 2010) "Fluidic timers for time-dependent, point-of-care assays on paper," Analytical Chemistry, 82(19):8071-8078.
Non-Final Office Action in U.S. Appl. No. 13/518,365, mailing date Oct. 3, 2014, 15 pages.
O'Farrell, B. (2009; retrieved Mar. 2016) "Evolution in Lateral Flow Immunoassay Systems," in *Lateral Flow-Based Immunoassay*, eds. R. Wong and H. Tse, Humana Press: New York, pp. 1-33.
Ohtake, S. and Wang, YJ (Jun. 2011) "Trehalose: Current Use and Future Applications," Journal of Pharmaceutical Sciences, 100(6):2020-2053.
Osborn, J. et al. (Oct. 2010) "Microfluidics without pumps: reinventing the T-sensor and H-filter in paper networks," Lab on a Chip, 10(20):2659-2665.
Park, Edward S. et al. (2010; retrieved Mar. 2016) "Packaging for Bio-micro-electro-mechanical Systems (BioMEMS) and Microfluidic Chips," in *Nano-Bio-Electronic, Photonic and MEMS Packaging*, C.P. Wong, Kyoung-Sik Moon, Yi Li (Eds.), Springer; pp. 505-563.
Patterson, K. et al. (Oct. 2002) "Development of a rapid immunodiagnostic test for Haemophilus ducreyi," Journal of Clinical Microbiology, 40(10):3694-3702.
Peeling, R. et al. (Dec. 2006) "Rapid tests for sexually transmitted infections (STIs): the way forward," Sexually Transmitted Infections, 82(Suppl 5):v1-v6.
Peltola V. et al. (Oct. 2005) "Accuracy of clinical diagnosis of influenza in outpatient children," Clinical Infectious Diseases, 41(8):1198-2000.
Peterson, LR and Diekema, DJ (Mar. 2010) "To Screen or Not to Screen for Methicillin-Resistant *Staphylococcus aureus*," Journal of Clinical Microbiology, 48(3):683-689.
Posthuma-Trumpie, GA et al. (Jan. 2009) "Lateral flow (immuno)assay: its strengths, weaknesses, opportunities and threats. A literature survey," Analytical and Bioanalytical Chemistry, 393(2):569-582.
Pribyl, M. et al. (Apr.-Sep. 2006) "Modeling reaction-transport processes in a microcapillary biosensor for detection of human IgG," Microelectronic Engineering, 83(4-9):1660-1663.
Qian, S.Z. and BAU, HH (Mar. 2004) "Analysis of lateral flow biodetectors: competitive format," Analytical Biochemistry, 326(2):211-224.
Rand, KH et al. (Jul. 2011) "A Comparison of Two Multiplex Methods for the Detection of Respiratory Viruses: FilmArray RP and xTAG RVP," Journal of Clinical Microbiology, 49(7):2449-2453.

(56) References Cited

OTHER PUBLICATIONS

Rejeb, S. et al. (Dec. 1998) "Functionalization of nitrocellulose membranes using ammonia plasma for the covalent attachment of antibodies for use in membrane-based immunoassays," Analytical Chimica Acta, 376(1):133-138.
Restriction Requirement for U.S. Appl. No. 13/518,365, mailing date Mar. 19, 2014, 6 pages.
Richardson, A. et al. (Mar. 2008) "A nitric oxide-inducible lactate dehydrogenase enables Staphylococcus aureus to resist innate immunity," Science, 319(5870):1672-1676.
Robinson, JM and Karnovsky, MJ (Jun. 1991) "Rapid-Freezing Cytochemistry—Preservation of Tubular Lysosomes and Enzyme-Activity," Journal of Histochemistry and Cytochemistry, 39(6):787-792.
Rojas, E. and Liu, L. (May 2005) "Estimating the annual hospital excess cost of methicillin-resistant Staphylococcus aureus infection in the United States," in International Society for Pharmaeconomics and Outcomes Research (ISPOR) Tenth Annual International Meeting, Washington, DC, 1 page.
Rossney, AS et al. (Oct. 2008) "Evaluation of the Xpert Methicillin-Resistant Staphylococcus aureus (MRSA) Assay Using the GeneXpert Real-Time PCR Platform for Rapid Detection of MRSA from Screening Specimens," Journal of Clinical Microbiology, 46(10):3285-3290.
Rubinstein, E. et al. (Jun. 2008) "Pneumonia caused by methicillin-resistant Staphylococcus aureus," Clinical Infectious Diseases, 46(Suppl 5): S378-S385.
Safdar, N. and Bradley, EA (Apr. 2008) "The risk of infection after nasal colonization with Staphylococcus aureus," American Journal of Medicine, 121(4):310-315.
Segall, G. and Purves, C. (1952; retrieved Mar. 2016) "The Action of Hydroxylamine, its o-methyl ether, and their Hydrochlorides on cellulose trinitrate in Pyridine," Canadian Journal of Chemistry, 30(11):860-871.
Sia, SK et al. (Jan. 2004) "An integrated approach to a portable and low-cost immunoassay for resource-poor settings," Angewandte Chemie (International Edition), 43(4):498-502.
Sigmundsson, K. et al. (Jul. 2002) "Determination of active concentrations and association and dissociation rate constants of interacting biomolecules: An analytical solution to the theory for kinetic and mass transport limitations in biosensor technology and its experimental verification," Biochemistry, 41(26):8263-8276.
Siwoski, A. et al. (Aug. 2002) "An efficient method for assessment of DNA quality of archival microdissected specimens," Modern Pathology, 15(8):889-892.
Skidmore, S. (Oct. 2010) "Poorly performing point-of-care tests for chlamydia: what can be done?" Sexually Transmitted Infections, 86(5):330-330.
Squires, TM and Quake, SR (Oct. 2005) "Microfluidics: Fluid physics at the nanoliter scale," Reviews of Modern Physics, 77(3):977-1026.
Stahlberg, A. et al. (Sep. 2004) "Comparison of reverse transcriptases in gene expression analysis," Clinical Chemistry, 50(9):1678-1680.
Stevens, D. (Aug. 2010) "Development and Optical Analysis of a Microfluidic Point-of-Care Diagnostic Device," Ph.D. thesis, University of Washington: Seattle, Washington, 230 pp.
Stevens, DY et al. (Dec. 2008) "Enabling a microfluidic immunoassay for the developing world by integration of on-card dry-reagent storage," Lab on a Chip, 8(12):2038-2045.
Sudhakar, D. et al. (May 1979) "Grafting of methyl methacrylate to nitrocellulose by ceric ions," Journal of Applied Polymer Science, 23(10):2923-2928.
Suk, JW and Cho, J-H. (Apr. 2007) "Capillary flow control using hydrophobic patterns," Journal of Micromechanics and Microengineering, 17(4):N11-N15.
Tanriverdi, S. et al. (Apr. 2010) "A rapid and automated sample-to-result HIV load test for near-patient application," Journal of Infectious Diseases, 201(Supplement 1):s52-s58.
Thompson, WW et al. (Jan. 2003) "Mortality associated with influenza and respiratory syncytial virus in the United States," JAMA—Journal of the American Medical Association, 289(2):179-186.
Thompson, WW et al. (Sep. 2004) "Influenza-associated hospitalizations in the United States," JAMA—Journal of the American Medical Association, 292(11):1333-1340.
Unger, MA et al. (Apr. 2000) "Monolithic microfabricated valves and pumps by multilayer soft lithography," Science, 288(5463):113-116.
Uyeki, TM et al. (May 2009) "Low Sensitivity of Rapid Diagnostic Test for Influenza," Clinical Infectious Diseases, 48(9):E89-E92.
Vasoo, S. et al. (Oct. 2009) "Rapid Antigen Tests for Diagnosis of Pandemic (Swine) Influenza A/H1N1," Clinical Infectious Diseases, 49(7):1090-1093.
Vijayendran, RA et al. (Dec. 1999) "A computational reaction-diffusion model for the analysis of transport-limited kinetics," Analytical Chemistry, 71(23):5405-5412.
Wakeley, PR et al. (Feb. 2010) "Use of a field-enabled nucleic acid extraction and PCR instrument to detect BVDV," Veterinary Record, 166(8):238-239.
Walker, GT et al. (Jan. 1996) "DNA detection by strand displacement amplification and fluorescence polarization with signal enhancement using a DNA binding protein," Nucleic Acids Research, 24(2):348-353.
Walkey, AJ et al. (May 2011) "Linezolid vs Glycopeptide Antibiotics for the Treatment of Suspected Methicillin-Resistant Staphylococcus aureus Nosocomial Pneumonia: A Meta-analysis of Randomized Controlled Trials," Chest, 139(5):1148-1155.
Wang, G. et al. (Apr. 2003) "Amperometric hydrogen peroxide biosensor with sol-gel/chitosan network-like film as immobilization matrix," Biosensors and Bioelectronics, 18(4):335-343.
Wang, W. et al. (Jun. 2010) "Tree-shaped paper strip for semiquantitative colorimetric detection of protein with self-calibration," Journal of Chromatography A, 1217(24):3896-3899.
Washburn, EW (Mar. 1921) "The Dynamics of Capillary Flow," Physical Review, 17(3):273-283.
Wellinghausen, N. et al. (Aug. 2009) "Rapid detection of Staphylococcus aureus bacteremia and methicillin resistance by real-time PCR in whole blood samples," European Journal of Clinical Microbiology and Infectious Diseases, 28(8):1001-1005.
Williams, MS et al. (Jul. 2008) "A practical guide to the staggered herringbone mixer," Lab on a Chip, 8(7):1121-1129.
Williams, R. (Jan. 1981) "The capillary without walls," Journal of Colloid Interface Science, 79(1):287-288.
Witkop, CT et al. (Feb. 2010) "Novel Influenza A (H1N1) Outbreak at the US Air Force Academy Epidemiology and Viral Shedding Duration," American Journal of Preventive Medicine, 38(2):121-126.
Wolk, DM et al. (Mar. 2009) "Multicenter Evaluation of the Cepheid Xpert Methicillin-Resistant Staphylococcus aureus (MRSA) Test as a Rapid Screening Method for Detection of MRSA in Nares," Journal of Clinical Microbiology, 47(3):758-764.
Wolk, Dm et al. (Mar. 2009) "Rapid Detection of Staphylococcus aureus and Methicillin-Resistant S. aureus (MRSA) in Wound Specimens and Blood Cultures: Multicenter Preclinical Evaluation of the Cepheid Xpert MRSA/SA Skin and Soft Tissue and Blood Culture Assays," Journal of Clinical Microbiology, 47(3):823-826.
Yager, P. et al. (Aug. 2008)"Point-of-care diagnostics for global health," Annual Review of Biomedical Engineering, 10:107-144.
Yager, P. et al. (Jul. 2006) "Microfluidic diagnostic technologies for global public health," Nature, 442(7101):412-418.
Yan, J. et al. (Feb. 2009) "A gold nanoparticle-based microfluidic protein chip for tumor markers," Journal of Nanoscience and Nanotechnology, 9(2):1194-1197.
Yeh, CH et al. (Jan. 2009) "An immunoassay using antibody-gold nanoparticle conjugate, silver enhancement and flatbed scanner," Microfluidics and Nanofluidics, 6(1):85-91.
Zarakolu, P. et al. (Aug. 2002) "Preliminary evaluation of an immunochromatographic strip test for specific Treponema pallidum antibodies," Journal of Clinical Microbiology, 40(8):3064-3065.
Zhang, C. et al. (Apr. 2006) "Development of multianalyte flow-through and lateral-flow assays using gold particles and horseradish

(56) References Cited

OTHER PUBLICATIONS peroxidase as tracers for the rapid determination of carbaryl and endosulfan in agricultural products," Journal of Agricultural and Food Chemistry, 54(7):2502-2507.

Zhao, W. and Van Den Berg, A. (Dec. 2008) "Lab on paper," Lab on a Chip, 8(12):1988-1991.

Zhao, WA et al. (Nov. 2008) "Paper-Based Bioassays Using Gold Nanoparticle Colorimetric Probes," Analytical Chemistry, 80(22):8431-8437.

Zhu, HY et al. (Jan. 2011) "Cost-effective and compact wide-field fluorescent imaging on a cellphone," Lab on a Chip, 11(2):315-322.

Zimmermann, M. et al. (Feb. 2009) "Autonomous capillary system for one-step immunoassays," Biomedical Microdevices, 11(1):1-8.

Zimmermann, M. et al. (Jan. 2007) "Capillary pumps for autonomous capillary systems," Lab on a Chip, 7(1):119-125.

Zimmermann, M. et al. (Mar. 2005) "Continuous flow in open microfluidics using controlled evaporation," Lab on a Chip, 5(12):1355-1359.

Zimmermann, M. et al. (Sep. 2008) "Valves for autonomous capillary systems," Microfluidics and Nanofluidics, 5(3):395-402.

Zinderman, CE et al. (May 2004) "Community-acquired methicillin-resistant *Staphylococcus aureus* among military recruits," Emerging Infectious Diseases, 10(5):941-944.

International Search Report and Written Opinion mailed Jun. 9, 2011, in International Application No. PCT/US2010/061675.

Office Action mailed May 5, 2016 in Chinese Patent Application No. 201480017562.5, 10 pages.

\* cited by examiner

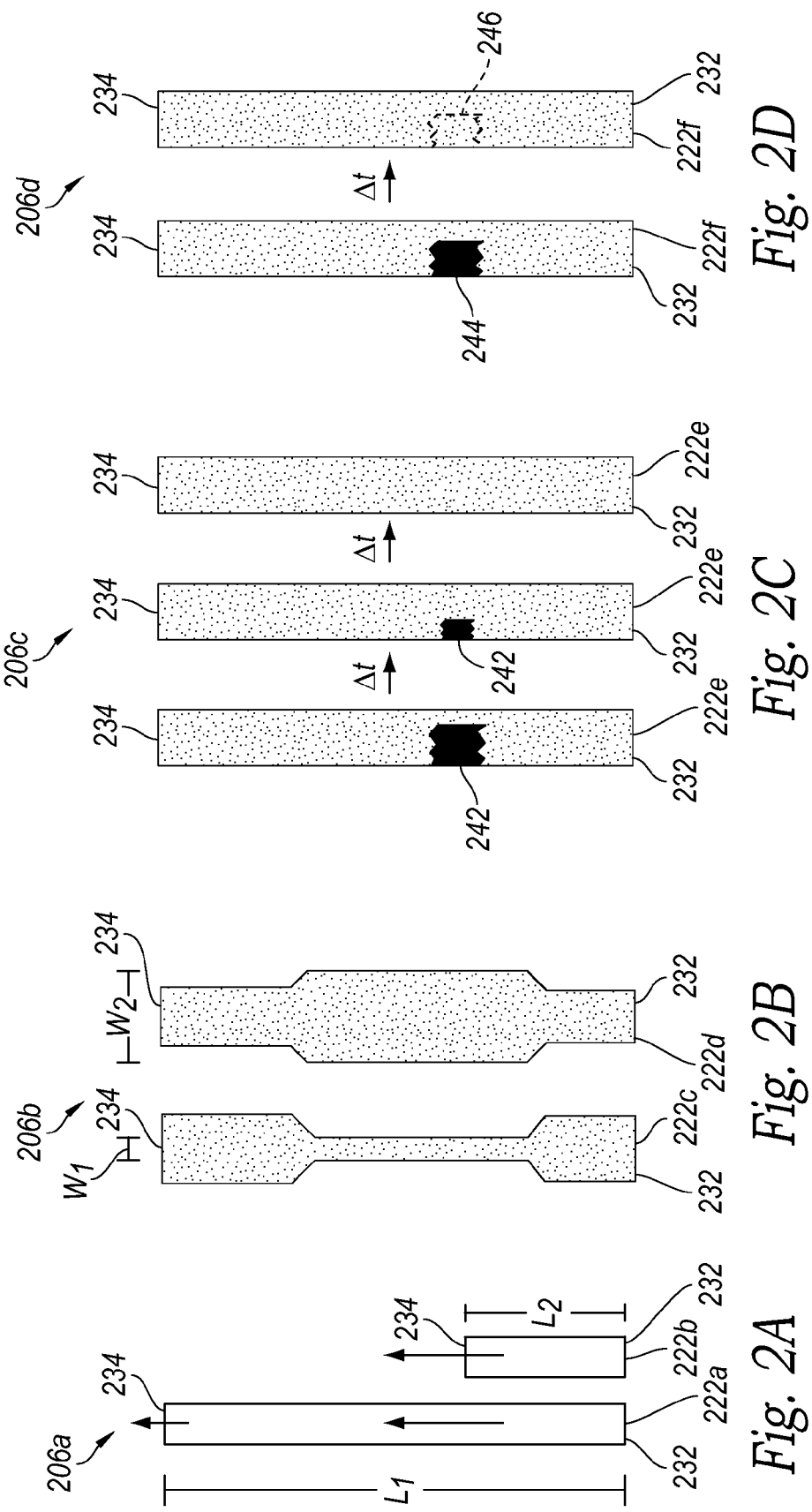

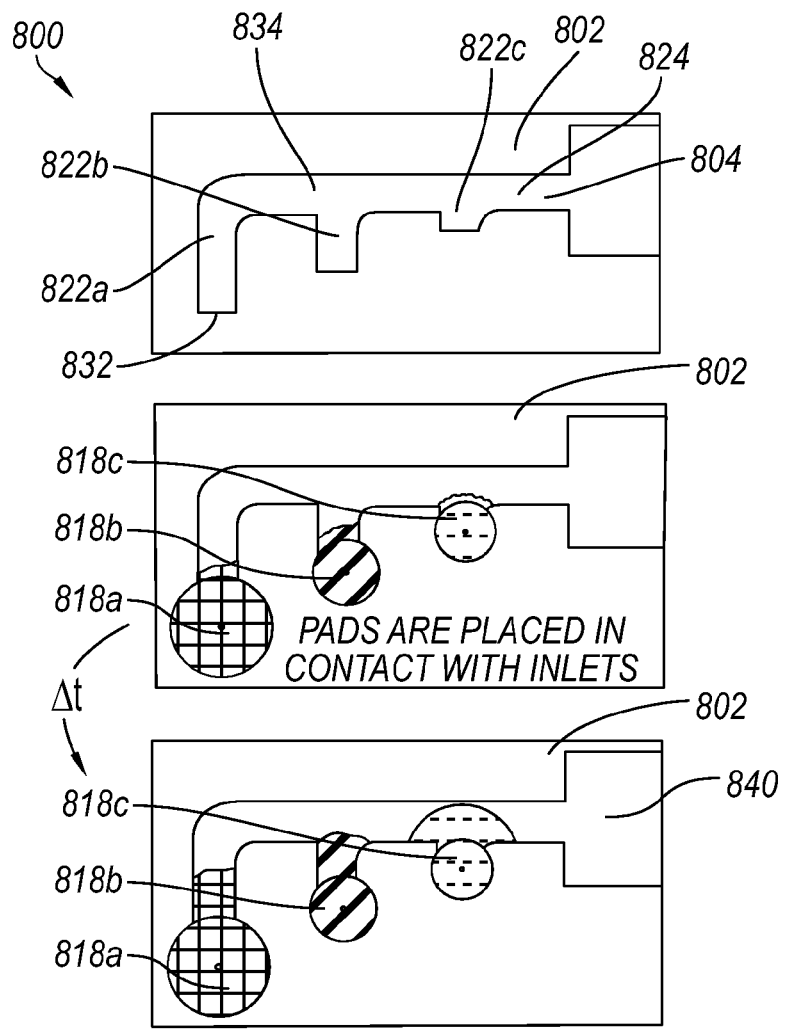
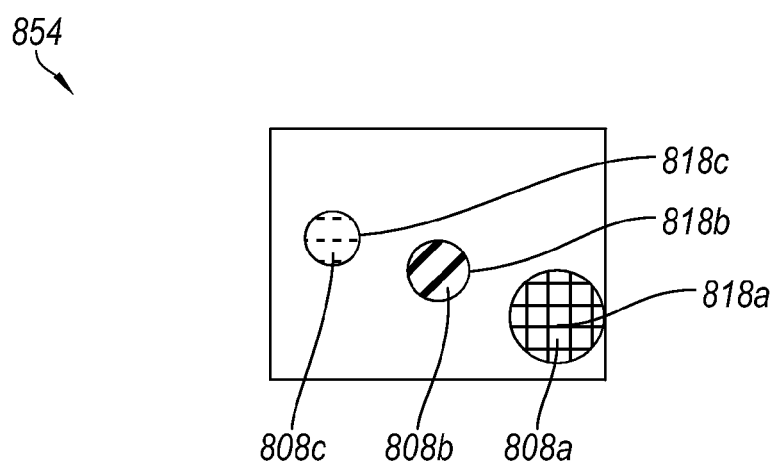

* TIME PASSED SINCE WETTING OF FIRST SPOT

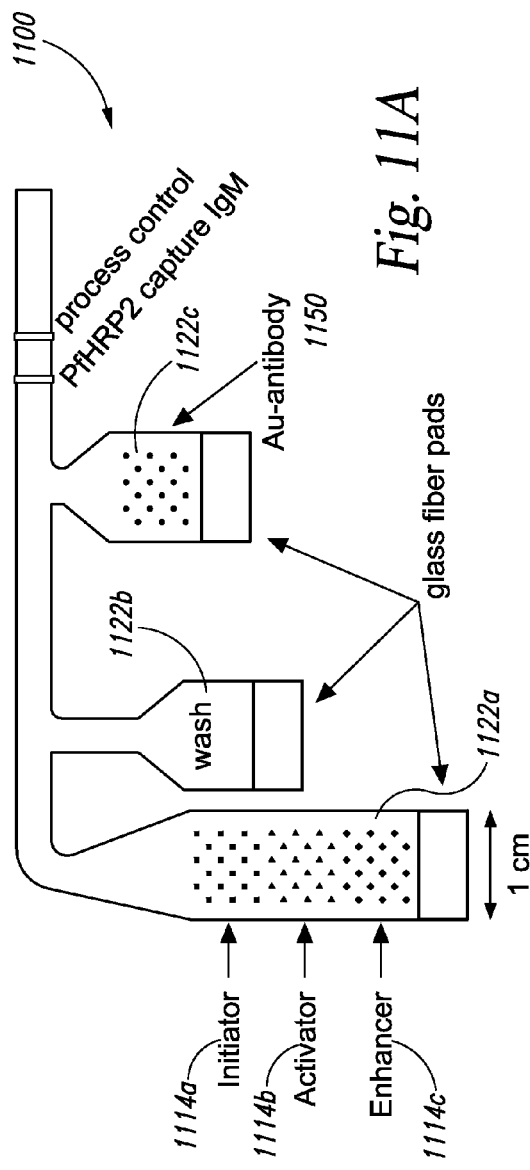
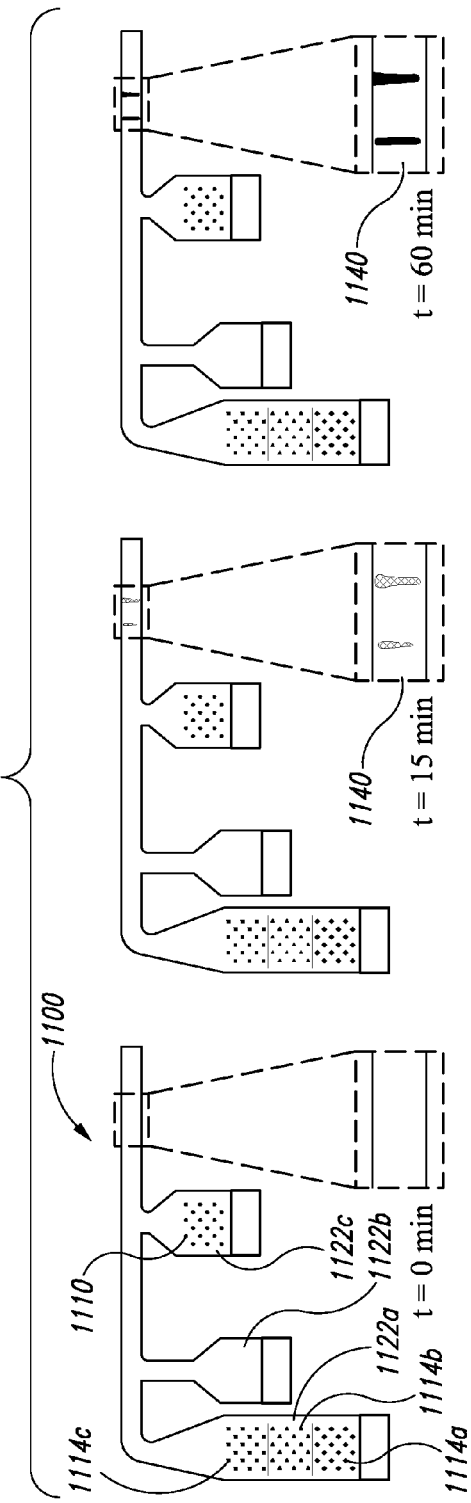
Fig. 11A
Fig. 11B

REAGENT PATTERNING IN CAPILLARITY-BASED ANALYZERS AND ASSOCIATED SYSTEMS AND METHODS

CROSS-REFERENCE TO RELATED APPLICATION(S)

This application is a U.S. national phase of international application No. PCT/US2012/044060, filed Jun. 25, 2012, which claims the benefit of U.S. Provisional Patent Application No. 61/501,055, filed Jun. 24, 2011, and U.S. Provisional Patent Application No. 61/609,667, filed Mar. 12, 2012, both of which are incorporated herein by reference in their entireties.

TECHNICAL FIELD

The present technology is generally related to capillarity-based devices for performing chemical processes and associated systems and methods. In particular, several embodiments are directed toward a capillarity-based device that makes use of reagent patterning techniques to provide control over microfluidic analyses.

BACKGROUND

Porous membranes are often used in conventional lateral flow and flow-through cartridges, in which flow of fluid occurs by wicking through the membrane (either laterally or transversely) onto an absorbent pad. Immunoassays take advantage of porous wick systems to measure and analyze analyte samples. The dependence on wicking to generate flow greatly limits control over assay conditions. Specifically, lateral flow assays are often limited to a single step in which sample (and buffer) is added to the sample pad, and the sample flows by capillary action (i.e., wicking) along the pad. Capillarity provides the force needed to provide a nearly continuous flow of fluid from one point to another, causing reagents stored in dry form to be transported along the device and to pass over regions that contain immobilized capture molecules. These devices are restricted to simple one-shot detection chemistries like colored nanoparticles that do not provide the sensitivity possible with multistep-detection chemistries, such as enzymatic amplification.

Microfluidic systems that include open fluid channels for the flow of buffers, samples, and reagents can inherently be made much more sophisticated, and it is possible to use them to carry out a very large number of fluid-processing steps. Such microfluidic systems usually incorporate a complex disposable, which leads to unavoidably high per-test manufacturing costs and the need for expensive external pumps and valves to move fluids. While microfluidic devices can inherently be very flexible in the functions that they perform, they are also inherently complicated and expensive. Additionally, the devices that have been made that support complex function are usually quite complex themselves. For example, some polymeric laminate cartridges currently developed contain as many as 23 different layers, each of which must be separately manufactured and bonded to the others.

BRIEF DESCRIPTION OF THE DRAWINGS

FIG. 2A is a front view of a flow-metering element configured in accordance with an embodiment of the technology.

FIG. 2B is a front view of a flow-metering element configured in accordance with an embodiment of the technology.

FIG. 2C is a series of time-lapsed front views of a pathway having a flow-metering element configured in accordance with an embodiment of the technology.

FIG. 2D is a series of time-lapsed front views of a pathway having a flow-metering element configured in accordance with an embodiment of the technology.

FIG. 8A is a series of time-lapsed front views of a capillarity-based device configured in accordance with an embodiment of the technology.

FIG. 8B is a front view of pre-wetted source pads for use with the device of FIG. 8A.

FIG. 11A is a schematic illustration of a capillarity-based device having a series of reagents printed thereon configured in accordance with embodiments of the technology.

FIG. 11B is a series of time-lapsed front views of the capillarity-based device of FIG. 4A configured in accordance with embodiments of the technology

DETAILED DESCRIPTION

Figure 1A:
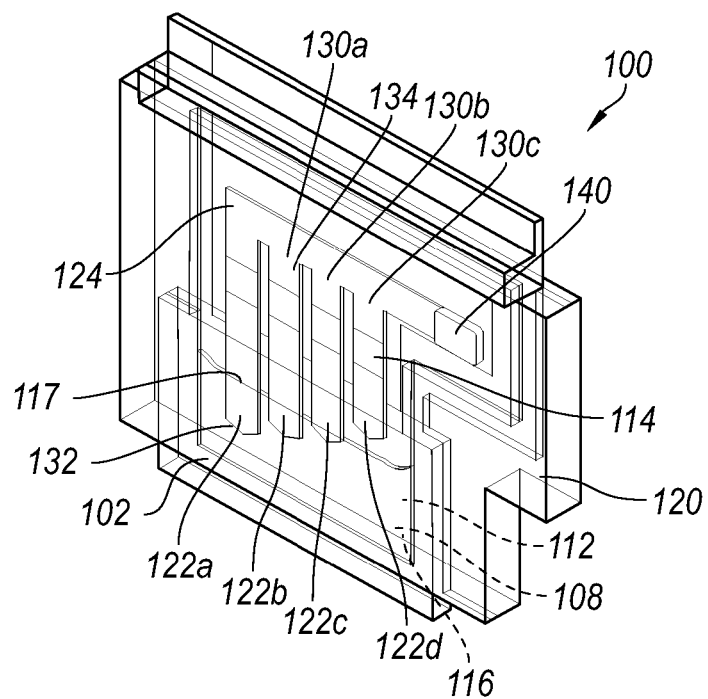
FIG. 1A is an isometric view of a capillarity-based device configured in accordance with an embodiment of the technology.

The present technology describes various embodiments of devices for processing, analyzing, detecting, measuring, and separating fluids. The devices can be used to perform these processes on a microfluidic scale, and with control over fluid and reagent transport. In one embodiment, for example, a device for performing chemical processes can include a porous wick comprising a pathway defined by an input end, an output end, and a length between the input end and the output end. The pathway is configured to wick fluid from the input end to the output end by capillary action. The device can further include a reagent placed on the pathway. For example, the reagent can be placed in a pattern configured to control a spatial or temporal distribution of the reagent along the pathway upon wetting of the pathway.

Specific details of several embodiments of the technology are described below with reference to FIGS. 1A-13B. Other details describing well-known structures and systems often associated with capillarity-based devices, biomedical diagnostics, immunoassays, etc. have not been set forth in the following disclosure to avoid unnecessarily obscuring the description of the various embodiments of the technology. Many of the details, dimensions, angles, and other features shown in the Figures are merely illustrative of particular embodiments of the technology. Accordingly, other embodiments can have other details, dimensions, angles, and features without departing from the spirit or scope of the present technology. A person of ordinary skill in the art, therefore, will accordingly understand that the technology may have other embodiments with additional elements, or the technology may have other embodiments without several of the features shown and described below with reference to FIGS. 1A-13B.

As used herein, the term "wick" refers to a material over which fluid can travel by capillary action. Typically, the wick is a porous membrane or matrix. Representative examples of such porous membranes include paper, nitrocellulose, nylon, and many other materials recognized by those skilled in the art as capable of serving as a wick in the context of the present technology. The wick can be two-dimensional or three-dimensional (when considering its height in addition to its length and width). In some embodiments, the wick is a single layer, while in other embodiments, the wick comprises two or more layers of membrane.

As used herein, the term "pathway" or "leg" refers to an elongated wick having a length greater than its width. Because the pathway is membranous, fluid traverses the pathway via capillary action or wicking. The width of the pathway is defined by sides or edges that limit the area of the pathway that can be traversed by fluid. Pathways can be patterned on a wick either by cutting the wick or by deposition of an insoluble barrier to create the desired configuration of pathways and pathway intersection(s).

As used herein, the term "wettably distinct" means being capable of being wetted by contact with separate fluids without mixing of the fluids at the point of initial wetting. For example, two input legs are wettably distinct if they are physically separated so that each leg could be brought into contact with a separate fluid reservoir. Pathways can be made wettably distinct by a variety of means including, but not limited to, separation via distinct edges (e.g., cut as separate pathways) and separation via an impermeable barrier.

A. Capillarity-Based Devices and Associated Systems and Methods

Figure 1B:
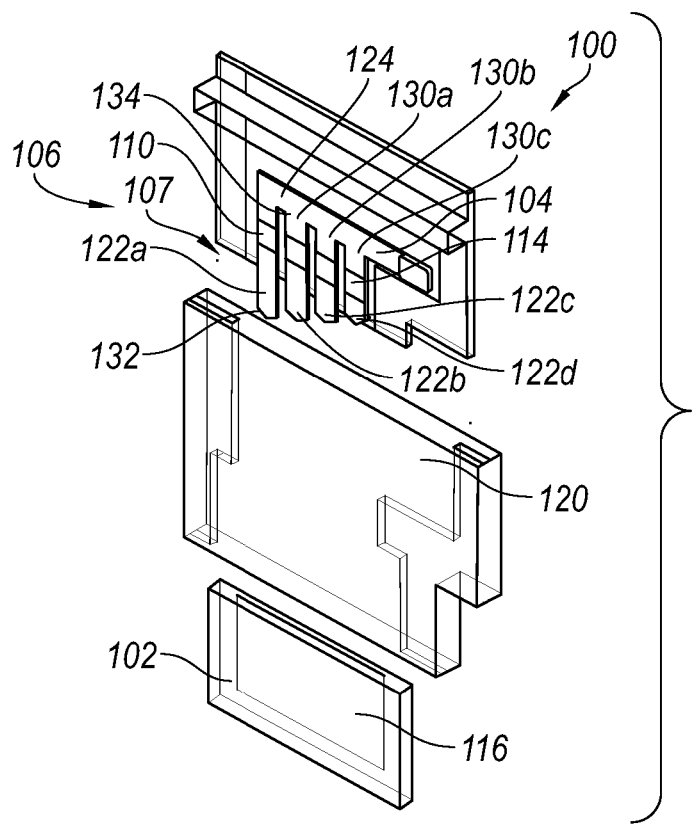
FIG. 1B is an exploded isometric view of the device of FIG. 1A.

FIG. 1A is an isometric view of a capillarity-based device or analyzer 100 configured in accordance with an embodiment of the technology, and FIG. 1B is an exploded isometric view of the device 100. Referring to FIGS. 1A and 1B together, the device 100 can include a base or housing 102 configured to support or interface with a porous matrix or wick 104. The wick 104 can further include one or more flow-metering elements 106 and/or volume-metering features 107. The flow-metering element 106 and volume-metering features 107 are configured to automatically and independently control or modify a rate or volume of fluid flow along the porous wick 104. In the illustrated embodiment, the flow-metering element 106 includes pathways 122 having differing lengths with corresponding differing flow rates. In some embodiments, the flow-metering elements 106 can regulate timing of fluid arrival at one or more intersection points 130 or detection regions 140 in the device 100.

The volume-metering features 107 can control the volume and timing of fluid delivery to the input ends 132 of each pathway 122. In the illustrated embodiment, for example, the volume of fluid supplied and shut-off time for each pathway 122 is controlled by the relationship between the position of the input end 132 of each pathway 122 and a level of fluid 108 brought into contact with the input end 132, e.g., via submersion in a fluid-filled well 116. Specifically, the well 116 stops contacting, and therefore stops supplying fluid to, pathways or legs 122 that extend a shorter distance below a surface 117 of fluid 108 in the well 116 than legs 122 that extend a longer distance below the surface of fluid 117 in the well 116. In other embodiments, other mechanisms can be used to control volume and timing. In one embodiment, for example, volume-limited fluid-delivery pads can be used. In another embodiment, wells 116 can contain different volumes of source fluid 108 and can supply these different volumes to individual legs 122. In some embodiments, one pathway 122a can be wetted simultaneously with another pathway 122b. In other embodiments, however, the pathway 122a can begin or end wicking before or after another pathway 122b. In still further embodiments, the wick 104 (or portions of the wick) can have a limited fluid capacity, thereby serving as another means to regulate volume. Further details regarding flow-metering elements 106 and volume-metering features 107 are described below with reference to FIGS. 2A-8C.

The base or housing 102 can be configured to receive one or more fluids 108 (FIG. 1A), such as a sample, inert fluid, or fluid reagent. In some embodiments, the base 102 can include one or more fluid wells or portals 116 configured to receive the fluids 108. Individual wells 116 can contain the same or different fluids. In other embodiments, these wells 116 can be absent and fluid can be supplied to the device 100 by other methods described in further detail below. The base 102 can be configured to support or carry the porous wick 104 in a vertical or horizontal orientation, or at an angle between the vertical or horizontal planes. In one embodiment, for example, the base 102 carries the wick 104 at an angle from about 45 degrees to about 90 degrees relative to the horizontal plane. The base 102 may further include an enclosure 120 that at least partially covers or surrounds the wick 104. In addition to providing structural support to the wick 104, the base 102 can further serve to protect the wick 104 from contamination, prevent evaporation of fluids 108 from the wick 104, and control humidity or other environmental conditions. The base 102 can be made of plastic, metal, glass, other materials, or a combination of materials. In further embodiments, the base 102 may be absent and the wick 104 can be unsupported or supported by another type of substrate.

In the illustrated embodiment, the wick 104 includes a plurality of pathways or legs 122a-122d (collectively "pathways 122"). Each pathway 122a-d has an input end 132, an output end 134, and a length between the input end 132 and the output end 134. Each pathway 122a-d can further include a width defined by two sides. The input ends 132 of the individual pathways 122a-d can be wettably distinct from one another. Pathways 122 or portions thereof can be generally straight or curved. In some embodiments of the technology, for example, at least one pathway 122 is non-linear. A serpentine pathway, for example, can zigzag via a series of curves, hairpin turns, sharp angles, or combinations thereof.

The pathways 122a-d intersect and converge into a common pathway 124. Two or more of the pathways can converge at the same or different locations or intersections 130a-130c (collectively "intersections 130") along the wick 104. Intersections 130 between pathways 122 can be at right angles or at larger or smaller angles. In some embodiments, for example, there may be a primary or first pathway 122a and a primary or first intersection 130a at which the primary or first pathway 122a converges with a secondary or second pathway 122b. In other embodiments, not all the pathways 122 need necessarily intersect. In still other embodiments, the merged pathways 122 can diverge into at least two pathways having wettably distinct output ends 134. In this latter embodiment, larger particles can be separated from a sample fluid in order to facilitate analysis of smaller analyte particles. In various embodiments that will be discussed in more detail below, fluid(s) 108 can travel and/or admix along pathways 122 and through intersections 130 simultaneously or sequentially.

The wick 104 can be composed of various materials including, for example, paper. In some embodiments, the wick 104 can be composed of backed nitrocellulose cut by a $CO_2$ laser. In some embodiments, the wick 104 have a thickness of about 0.120 mm or greater. The wick 104 can be given a desired pathway configuration by printing onto the wick 104 or by cutting the wick 104. Cutting the wick 104 can be performed by any of several low- or high-throughput methods, including computer-controlled knife cutters. Patterning of the pathways 122 on the wick 104 can be achieved, for example, by cutting the wick 104 and/or by treating the wick 104 to create pathways 122 that can be traversed by fluid 108. In one embodiment, for example, sides of the pathways 122 may be defined by the edge of the porous wick 104. In another embodiment, the sides of the pathways 122 may be defined by an insoluble (e.g., impermeable, hydrophobic) barrier.

In several embodiments, the device 100 is devoid of a pump. The need for a pump may be obviated by a design that enables all fluid movement to be effected via capillary action. In operation, capillary force can be generated by the wick 104 itself (i.e., as the fluid initially wets the wick 104), or the capillary force can be generated by an absorbent pad (not shown) at the output end 134 of an individual pathway 122 or the common pathway 124. In one embodiment, the porous wick 104 can have a pore size of from about 200 nm to about 30 μm. In a particular embodiment, the pore size of the wick is from about 5 μm to about 20 μm. In some embodiments, the wick 104 can have an effective surface area about 300 times larger than a flat surface, allowing for increased measurement sensitivity and rapid diffusion. In other embodiments, however, the wick 104 can have different dimensions and/or arrangements.

As noted above, the porous wick 104 is configured to wick one or more fluids (e.g., fluid(s) 108) from the input ends 132 toward the output ends 134 of the respective pathways 122 upon wetting of the pathways 122. In one embodiment, for example, the input ends 132 of the pathways 122 can contact the fluid 108 within the base 102, for instance, by submerging the wick 104 in the well 116 of the base 102. In another embodiment, a sample fluid can be applied to a pathway 122 before the wick 104 contacts the fluid reservoir 116. In this embodiment, the sample can flow solely by capillary action along the wick 104 or can be additionally pushed along the pathway 122 by upstream fluid 108 upon wetting the input end 134 of the pathway. In yet another embodiment, as discussed in more detail below with reference to FIGS. 7A-8C, the fluid(s) 108 can be placed directly on the wick 104 in the form of pre-wetted pads (not shown) or other means. In still further embodiments, the wick 104 can be wetted by a combination of these mechanisms. After wetting, the fluid(s) 108 travel along the wick 104 toward the detection region 140 where a chemical analysis is done or where results of the chemical analysis can be read by a user (not shown). In further embodiments, the wick 104 can include a sample receiving region, an extraction region (e.g., for extracting analytes), and/or an amplification region (e.g., for nucleic acid amplification).

The fluid traveling along each pathway 122 can include one or more samples (e.g., analytes) 110, fluid reagents, indicators, binding/capture agents, and/or wash solutions 112. The sample 110 can include blood, urine, saliva or other bodily fluid, or other non-bodily fluids. In some embodiments, one or more dried reagents 114 can be placed on or embedded along the wick 104, either directly or on a substrate. Reagents 114 can be spotted on the wick 104 manually, by vacuum during, through inkjet or piezoelectric printing, or by other methods. The reagents 114 can be immobilized on the wick 104 or can dissolve and become mobile upon contacting fluid 108 traveling along the wick. As will be discussed in further detail below with reference to FIGS. 9-13B, depending upon the reagent 114 patterning on the wick 104, the reagents 114 can exhibit various temporal and/or spatial distributions upon making fluidic contact with the fluid 108 entering the input ends 132 of the pathways 122. In still further embodiments, liquid reagents 114 can be used. For example, in one embodiment, approximately from about 3 μl to about 80 μl reagent 114 can be applied to the wick 104 or pad using a syringe or pipette.

In some embodiments, the device 100 further includes a capture agent (not shown) that binds the analyte 110 disposed on the wick 104 downstream of the primary intersection 130a. Capture agents can be used for either direct or competitive assays to determine the presence and/or quantity of analyte 110 present in a sample. Typically, the device 100 further comprises the reagent 114 disposed on one of the secondary pathways (e.g., pathway 122b). The reagent 114 can be located downstream of the primary intersection 130a. The reagent 114 can interact with the analyte 110 and/or the capture agent, and can be mobilized upon contact with the fluid 108. The positioning of reagents 114 as well as pathways 122 that will be traversed by inert fluid (e.g., water, buffer) can be designed to create an appropriate series (sequential or simultaneous) of chemical interactions and washes that allow for all steps of a conventional assay, such as an immunoassay or a nucleic acid amplification and detection, to be performed on the wick 104. For example, the configuration of the pathways 122 and intersections 130 and the use of reagent patterning can be used to control the sequence of assay steps to be performed. In one example, a series of secondary pathways 122b/122c/122d merges via a series of intersections 130a/130b/130c into a single secondary pathway 124 that, in turn, intersects with the primary pathway 122a. Because the assay steps are all initiated by the fluid traversing the wick 104 via capillary action, the only necessary step to activate the entire series of assay steps is the initial contact between the input ends 132 of the pathways 122 and the fluid 108.

The device 100 can be used for analyzing, diffusing, detecting, filtering, processing, measuring and/or separating fluid samples 110. The device 100 may also be used for solid-phase assay and selective capture. The device 100 can be used to perform these processes on a microfluidic scale, and with control over fluid and reagent transport within the device 100.

B. Select Embodiments of Flow-Metering Elements

FIGS. 2A-4 illustrate various embodiments of flow-metering elements configured in accordance with embodiments of the technology. The flow-metering elements described below, for example, can be used with the device 100 (FIGS. 1A and 1B) or other suitable capillarity-based devices. The flow-metering elements of FIGS. 2A-2D are configured to modify a rate or volume of fluid flow along a porous wick (e.g., wick 104 of FIGS. 1A and 1B). The flow-metering elements may be located on one or more fluid pathways (e.g., pathways 222) and before or after an intersection point (e.g., intersection(s) 130) where the pathways converge. In some embodiments, the flow-metering elements can be an integral component of a porous wick. In other embodiments, however, the flow-metering elements may be removable from the wick. Further, in some instances, two or more of the following examples of flow-metering elements can be used in conjunction or separately to obtain the desired rate and volume of fluid flow.

FIGS. 2A and 2B, for example, are front views of flow-metering elements 206a and 206b, respectively, configured in accordance with embodiments of the technology. In particular, the flow-metering elements 206a and 206b illustrated in FIGS. 2A and 2B statically modify the rate or volume of fluid flow in a device by modifying a geometric characteristic of one or more pathways 222. For example, the flow-metering element 206a of FIG. 2A modifies the rate or volume of fluid flow by adjusting the length of one or more pathways 222, while the flow-metering element 206b of FIG. 2B modifies the rate or volume of fluid flow by adjusting the width of one or more pathways 222. The flow velocity along a pathway 222 is proportional to the capillary force generated at the fluid front (C×Wf) and inversely proportional to the sum of resistances for the flow path (Sum(Wi/Li)). Accordingly, the overall flow velocity for a pathway 222 can be adjusted by adjusting the pathway length and/or the pathway width.

Referring first to FIG. 2A, varied leg length is used to control the rate of fluid flow along pathways 222a and 222b. In a segment of constant width, movement of the fluid front advancing into a dry membrane depends on the resistance that the wet paper behind it presents to flow of the lengthening column of fluid. This resistance increases with length, so the further the front moves, the slower it moves, according to the Washburn equation:

$$L^2 = \gamma Dt/4\mu',$$

where L is distance moved by the fluid front, t is time, D is the average pore diameter, γ is surface tension, and μ is viscosity. In the illustrated embodiment, a first pathway 222a has an extended length $L_1$ that extends the time required for fluid to travel the pathway 222a relative to a second, shorter pathway 222b having length $L_2$.

Referring next the FIG. 2B, the flow-metering element 206b comprises first and second pathways 222c and 222d having differing widths. Resistance decreases as the width of the segment increases, so the speed of the front depends on the width of the segment behind it. Accordingly, fluid rate and output volume can be controlled by manipulating individual pathway widths. For example, in the illustrated embodiment, a portion of the first pathway 222c has a narrowed width $W_1$ that shortens the time required for fluid to travel the length of the narrowed portion of the pathway 222c relative to a second, wider pathway 222d having a width $W_2$.

FIGS. 2C and 2D include a series of time-lapsed front views of pathways having flow-metering elements configured thereon in accordance with additional embodiments of the technology. More specifically, FIGS. 2C and 2D illustrate pathways 222e and 222f having flow-metering elements 206c and 206d, respectively, that include a barrier placed along the fluid pathway. The barriers can be dissolvable or soluble (as illustrated in FIG. 2C) or switchable (as illustrated in FIG. 2D). Dissolvable and switchable barriers can be used to dynamically modify the rate at which fluid moves through the wick.

Referring first to FIG. 2C, the pathway 222e has a soluble barrier 242 disposed thereon and positioned to block or hinder fluid flow along the pathway 222e. In one embodiment, the barrier 242 can dissolve over time after contacting fluid in the wick. By controlling the length, width, and material of the barrier 242, the rate and volume of fluid flow along the pathway 222e can be regulated. Longer and/or wider barriers 242 can hinder fluid flow for a longer amount of time than shorter/narrower barriers 242. Furthermore, dissolvable barriers 242 can differ in their solubilities or dissolution rates, such as by use of differing materials, e.g., salt, sugar, etc., or in differing mixtures or concentrations of materials. Soluble barriers 242 will be discussed further below with reference to FIGS. 3A-3D.

Referring next to FIG. 2D, the pathway 222f has a switchable barrier 244 disposed thereon and positioned to block or hinder fluid flow along the pathway 222f. In one embodiment, the switchable barrier 244 can be composed of a material that is hydrophilic at room temperature and hydrophobic upon heating, thereby altering the time required for fluid to travel the length of the pathway 222f in a heat-dependent manner. In an alternative embodiment, the material is hydrophobic at room temperature and hydrophilic upon heating. The flow-metering element 206d can further include one or more heating elements 246 disposed at one or more locations along or near the pathway 222f. The heating element 246 can be used to effect a switch between hydrophilic and hydrophobic states of a barrier 244 disposed on the wick. Alternatively, the material can switch between hydrophilic and hydrophobic with a change in pH or other property. The time required for fluid to travel the length of the pathway 222f can accordingly be controlled in a heat- or pH-dependent manner. Switchable barriers 244 will be discussed further below with reference to FIG. 4.

As discussed above, barriers can control the rate and volume of fluid delivery downstream of the barrier by serving as a physical blockade to fluid flow. Additionally, barriers can also be used to decrease the local resistance to flow over time. For example, dissolvable barriers 242 could be designed to give a constant flow velocity by decreasing the local resistance to counteract the increase in resistance due to the movement of the fluid front. Switchable barriers 244 can be used to actively change the local resistance. In some embodiments, described in further detail below with reference to FIGS. 3A-4, barriers can be used for precise timing of sequential delivery of sample, wash, and/or reagent to a detection region. While FIGS. 2C and 2D each illustrate only a single barrier in a single pathway, in other embodiments there can be more than one barrier in an individual pathway and/or barriers in multiple pathways within a device.

Figure 3A:
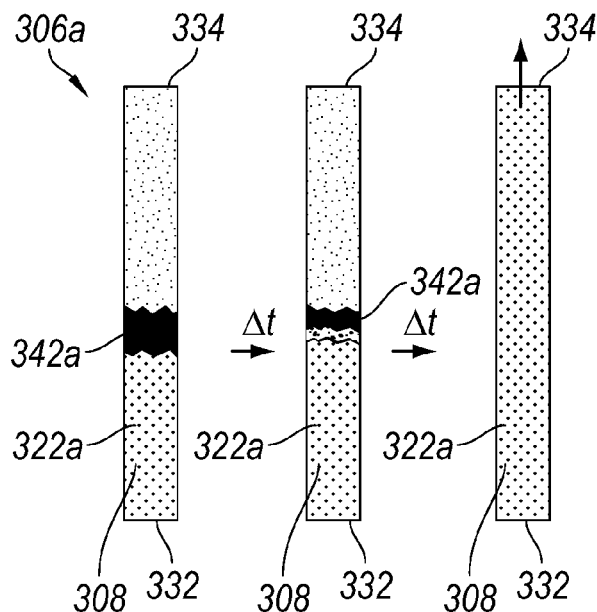
FIG. 3A is a series of time-lapsed front views of a pathway having a soluble barrier configured in accordance with an embodiment of the technology.

FIGS. 3A-3D illustrate capillarity-based devices or analyzers utilizing soluble barriers 342 as flow-metering elements 306. FIG. 3A, for example, illustrates a series of time-lapsed front views of a pathway 322a having a flow-metering element 306a configured in accordance with an embodiment of the technology. In this particular embodiment, the flow-metering element 306a includes a soluble material 342a that is deposited on the pathway 322a and dried such that it forms a barrier to fluid wicking during the assay. The solution of dissolvable material 342a can be deposited by various methods, including, for example, manual spotting, dipping the paper strip into the solution, use of striping instruments, and use of contact and non-contact spotting devices such as piezo spotters or pneumatic sprayers. When the assay is started, a fluid 308 wicks from an input end 332 of the pathway 322a up to the barrier 342a, which functions as a dam. The fluid 308 dissolves the soluble material over time and is then free to wick toward an output end 334 of the pathway 322a. The rate of dissolution and the size of the soluble barrier 342a determine the amount of delay time, and this can be different for each pathway 322a.

The soluble barrier 342a may be composed of any dissolvable material that is soluble in the assay fluid, including sugars, salts, gum Arabic, gel material, etc. Also, mixtures of these materials can be used to tune the barrier properties and precisely control fluid flow. For example, mixtures of trehalose (fast dissolving barrier material) and sucrose (slow dissolving barrier material) provide barriers with behavior between the two individual materials. In one embodiment, an absorbent pad (not shown) containing trehalose in water (~40% by weight) can be used to create a stripe of trehalose across a nitrocellulose wicking strip, which is then allowed to dry overnight. Trehalose is also effective as a protein preservative. The dissolvable materials can be reagents themselves, or reagents stored in dry form within soluble materials, for example a detection probe stored in a sugar matrix. In other embodiments, an inert (i.e., non-reagent) barrier 342 may be desired to prevent premature dissolution of the reagent on the downstream side of the barrier. Dry reagents could also be applied on pads or on the porous wick itself on the upstream side, where they would be able to dissolve into the fluid 308 during the timed dissolution of the soluble barrier 342.

Figure 3B:
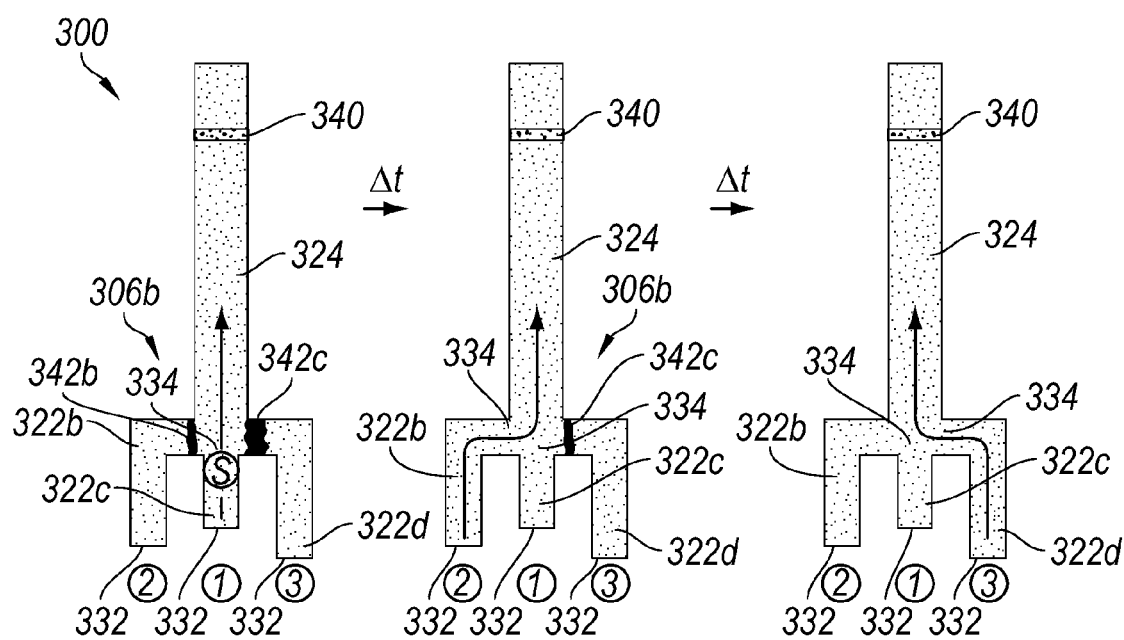
FIG. 3B is a series of time-lapsed front views of a capillarity-based device having a plurality of soluble barriers configured in accordance with an embodiment of the technology.

FIG. 3B is a series of time-lapsed front views of a capillarity-based device or analyzer 300 having a plurality of soluble barriers 342 (three are shown in the illustrated embodiment as soluble barriers 342a-c) configured in accordance with embodiments of the technology. In the illustrated embodiment, the device 300 has a plurality of pathways or legs (three are shown as pathways 322b, 322c, and 322d, and numbered 1-3). Each pathway 322b-d includes an input end 332. An analyte sample S is in the middle leg 322c, labeled "1" and reagent, sample, or wash solutions are in each of legs 2 and 3. To perform particular testing on the sample "S", it is desirable for the analyzer to first allow the sample to flow into a common channel 324, followed by fluid in leg 2, followed by fluid in leg 3. The assay can be used for ordered fluid commingling in the common channel 324 or for sequential, timed delivery of fluid to a detection region 340. This ordering can be implemented in a single user step by use of soluble barriers.

The device 300 can be placed into a fluid source (or otherwise wetted) which begins fluid wicking from input ends 332 toward the detection region 340. Since leg 1 has no soluble barriers or other flow-metering mechanisms, the sample S is simply wicked toward the detection region 340. Fluid is wicked along both leg 2 and leg 3, but is stopped by the respective soluble barriers 342b and 342c. The soluble barrier 342c of leg 3 is larger than the soluble barrier 342b of leg 2, so the soluble barrier 342c of leg 3 takes a greater time to dissolve. As shown in the second pane, fluid breaks through the soluble barrier 342b in leg 2 while the barrier 342c in leg 3 remains. The fluid from leg 2 is now being wicked along the common channel 324 toward the detection region 340. As shown in the third pane of FIG. 3B, the fluid has sequentially dissolved the barrier 342c in leg 3, allowing the fluid in leg 3 to wick toward the detection region 340. Accordingly, the soluble barriers 342b and 342c can serve to perform the chemical analyses under the pre-set timing constraints.

In some embodiments, the downstream side of a barrier 342 is wetted by other assay fluids and dissolution of the barrier 342 occurs from both sides of the barrier. The two fluids meet within the barrier 342, at which point the two fluids begin to move toward the detection region 340. In the illustrated embodiment, for example, fluid from both upstream and downstream sides of the barriers 342b and 342c in legs 2 and 3 works to dissolve the respective barriers. In other embodiments, a portion of a pathway 322 downstream of the soluble barrier 342 can be pre-wet with buffer to control and/or reduce commingling of fluids. In other embodiments, the device 300 can take on different geometric configurations, legs 322 and barriers 342 can be arranged to deliver fluid in different orders to a common channel 324, and there can be more or fewer legs 322 and/or barriers 342.

Figure 3C:
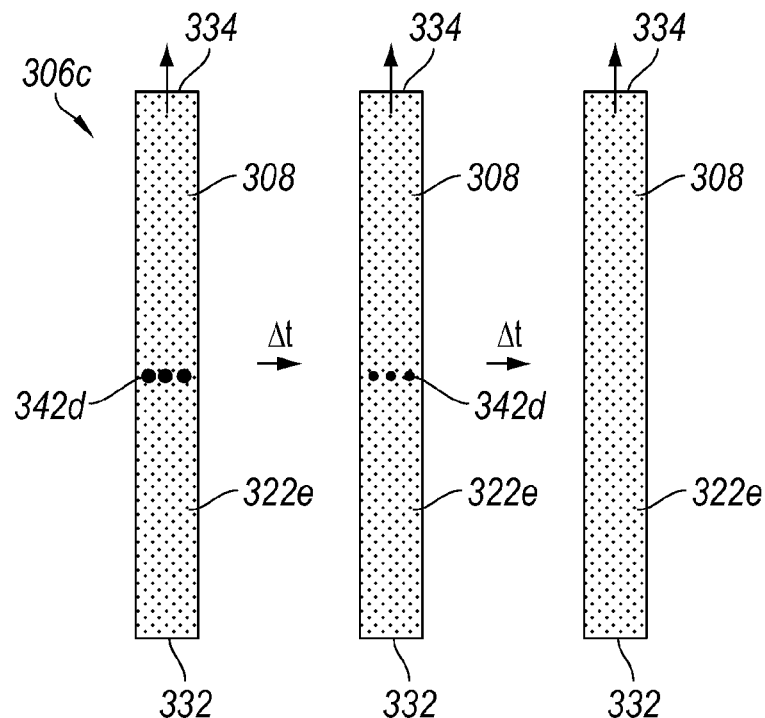
FIG. 3C is a series of time-lapsed front views of a pathway having a soluble restrictor configured in accordance with an embodiment of the technology.

FIG. 3C is a series of time-lapsed front views of a flow-metering element 306c having a soluble restrictor 342d configured in accordance with another embodiment of the technology. In the illustrated embodiment, the soluble material 342d is patterned to initially span only a portion of the width of a pathway 322e. Similar to the barriers discussed above with reference to FIGS. 2C, 3A, and 3B, the soluble restrictor 342d serves to limit the rate of fluid flow from an input end 332 toward an output end 334 along a pathway 322e. The difference between the embodiment shown in FIG. 3C and those described above, however, is that restrictors 342d always allow some fluid to pass through the pathway. Thus, flow is only slowed, not entirely stopped, for the time period before the dissolution. As shown in FIG. 3C, for example, the restrictors 342d dissolve over time and an open fluid pathway 322e remains. Fluid is continuously supplied from a fluid source (not shown) to surround the restrictor 342, and dissolution occurs faster than it would in the case of stopped flow.

Figure 3D:
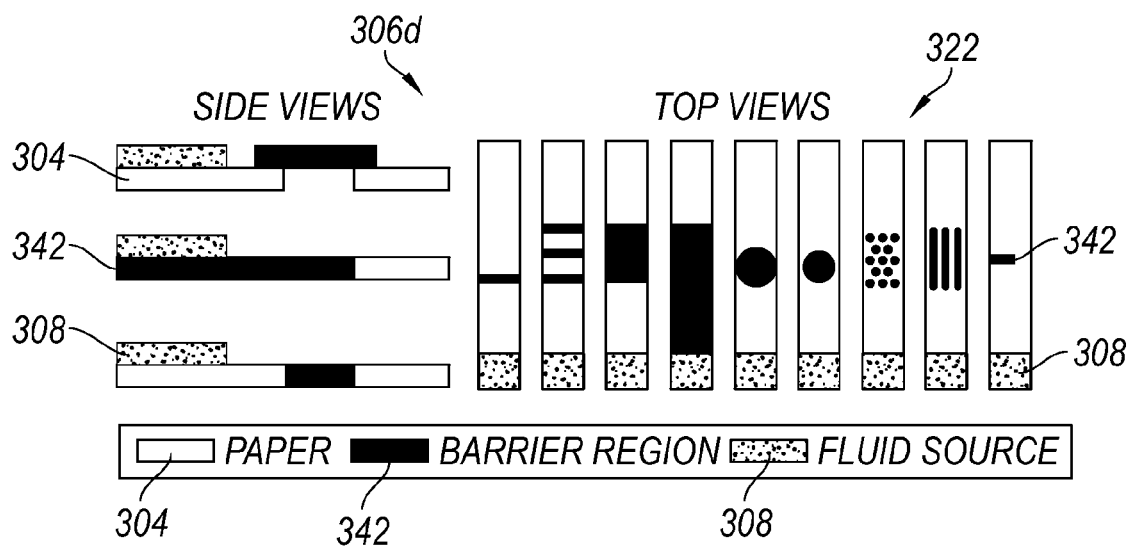
FIG. 3D is a series of front views of pathways having soluble barriers or soluble restrictors configured in accordance with embodiments of the technology.

FIG. 3D is a series of side and front views of flow-metering elements 306d comprising various shapes of soluble barriers and soluble restrictors (collectively "soluble barriers") 342 deposited on pathways 322 and configured in accordance with further embodiments of the technology. As the illustrated examples indicate, there are countless arrangements of soluble barriers 342, and choosing one simply depends on the timing requirements of the particular assay. In some embodiments, for example, the dissolvable material 342 can be deposited on a separate strip of paper 304 or other support that is then added to create a bridge between two parts of the device. The shape and size of the barrier 342 can be varied to tune the dissolution pattern and fluid 308 breakthrough time. In other embodiments, a plurality of barriers 342 in series or in parallel delays the fluid flow more than if only a single barrier 342 was used. Again, the length and/or width of a barrier 342 also affect the rate of fluid flow.

Referring to the soluble barriers 342 of FIGS. 3A-3D collectively, a significant difference of the use of dissolvable barriers over extending the leg length to create delays in reagent arrival at the detection region is that after dissolution, the reagent can have a high average flow rate that is characteristic of flow in the material at small distances from the fluid source since the overall path length of reagent in the device can be kept small. In contrast, delays created by extension of the leg length will result in a lower average flow rate due to the low flow rates characteristic of flow at large distances from the fluid source.

Larger concentrations of deposited dissolvable material lead to reduced voids and tend to reduce flow to a greater extent than smaller concentrations of the same dissolvable material. For example, saturated sucrose or table sugar creates a nearly impenetrable barrier that stops or greatly slows advance of the fluid, while lower concentrations of sucrose include voids that allow continuous, yet slowed, advance of the fluid through the barrier. Different sugars have different levels of saturation (as a weight percent) and give qualitatively different wetting behavior. For example, barriers created by saturated trehalose or glucose are more easily penetrated than barriers created by saturated solutions of sucrose or table sugar.

The dissolvable materials can also affect the viscosity and surface tension of the assay fluid, and thus influence the flow rate. Different dissolvable materials have different effects on these two properties, and high concentration solutions have the largest effects. Restrictions result in lower concentration compared to barriers that span the width of the leg. Since the surface tension is a critical parameter in the Washburn equation, if the solute changes the surface tension of the fluid, the flow downstream of the barrier or restriction can be different than upstream of the barrier. The effect of surface tension is greatest when the paper downstream of the barrier or restriction is dry, and the effect of surface tension is less when the paper downstream is wetted. The effect of viscosity can be significant in both cases. Additives to the dissolvable material can be used to affect these properties. For example, addition of surfactant can reduce the surface tension.

The delay created by a dissolvable barrier or restriction may be varied in many ways, including the dissolution rate of the dissolvable material, the concentration of the deposited solution of dissolvable material, the total expanse of paper treated with the dissolvable material (i.e., the length of a barrier), and/or the shape of the resulting barrier or restriction. All of the variations described above can be used to create a range of delays in a single device. For example, using only simple sugars (trehalose, glucose, sucrose, and table sugar), delays from seconds to an hour or more can be created. For long delays, evaporation of the fluid can affect the delay timing or even lead to stalling of the fluid when the evaporation rate matches the fluid supply rate. High humidity can be created by enclosing the paper in a device with liquid present.

Dissolvable barriers and restrictions can be used to delay the delivery of a reagent to a common fluid channel, and they can also be used to delay movement of fluid into an upstream or a downstream path. For example, a barrier or restriction can be used to open a pathway to an absorbent pad to increase overall flow, to initiate flow, or to reverse the flow through a leg. In the latter case (reversing the flow), a barrier can be timed to coincide with an upstream absorbent pad reaching its fluid capacity, allowing fluid to reverse direction by flowing into the absorbent pad opened by a dissolvable barrier.

Figure 4:
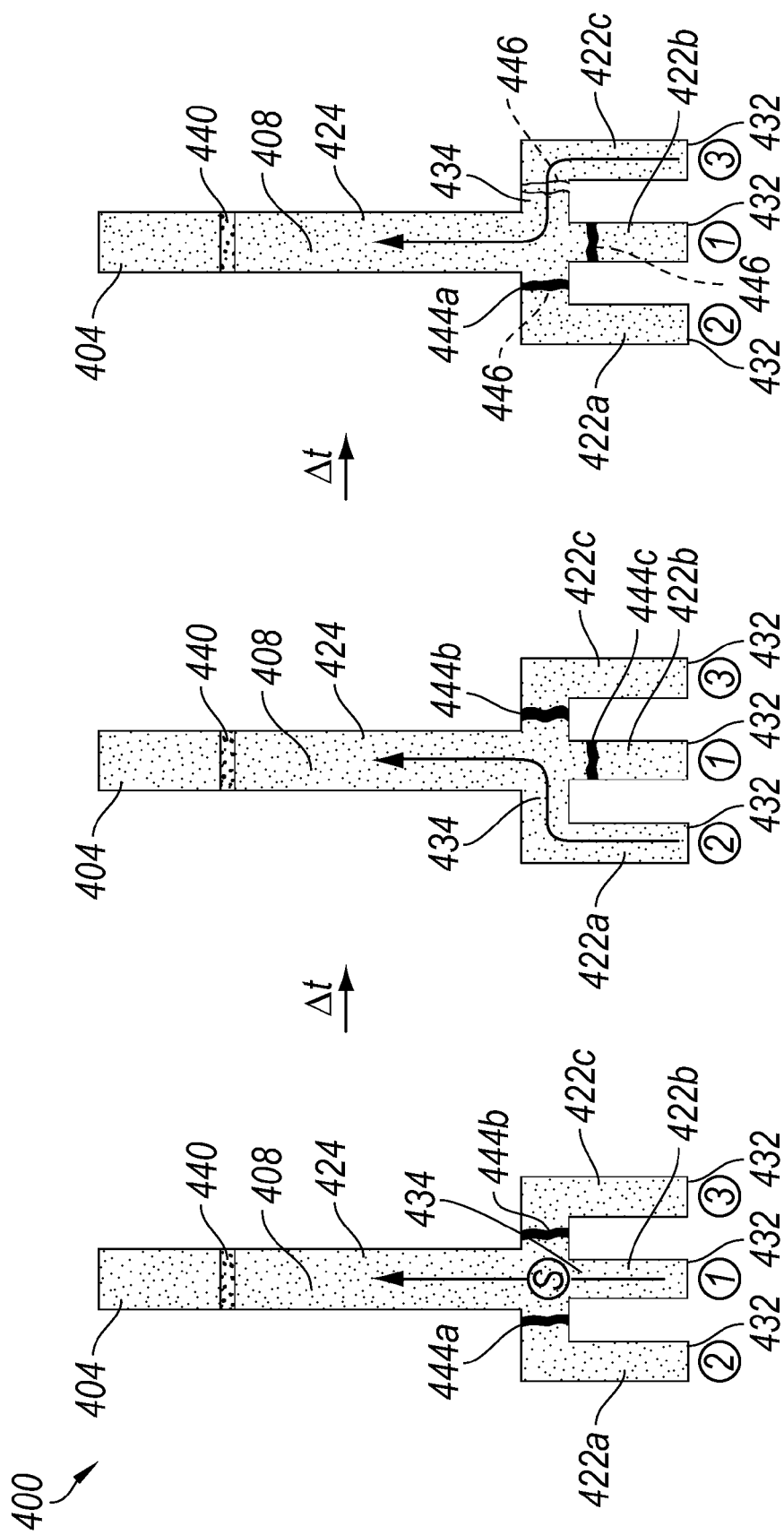
FIG. 4 is a series of time-lapsed front views of a capillarity-based device having a plurality of switchable barriers configured in accordance with an embodiment of the technology.

FIG. 4 is a series of time-lapsed front views of a capillarity-based device or analyzer 400 having a plurality of switchable barriers 444a-444c (collectively "switchable barriers 444") configured in accordance with an embodiment of the technology. The device 400 has several features generally similar to the device 300 described above with reference to FIG. 3B. Instead of having soluble barriers 342, however, the device 400 includes material 444 capable of switching between hydrophobic and hydrophilic states patterned on pathways 422a-422c (collectively 422) of a wick 404. The switchable barrier 444 serves as a "gate" to control the timing of fluid flow along the wick 404. In one embodiment, for example, a material (e.g., poly-NiPAAm), can switch between hydrophilic and hydrophobic states via changes in temperature or pH. In other embodiments, other switchable materials can be used. A heating element 446 (shown schematically) positioned near the gates 446 serves as a switch. Independently controlled switches can be used for each liquid and/or leg 422.

In the illustrated embodiment, the device 400 has three gates 444a-444c, one on each of the legs 422. The legs 422 are numbered 1-3 in the order that fluids 408 within the legs 422 should be wicked toward a detection region 440 in order to perform a particular assay. In the first pane, the gates 444a and 444b of legs 2 and 3, respectively are closed, while the gate 444c on leg 1 is open allowing fluid 408 in leg 1 (including a sample S) to wick toward the detection region 440. The heating element 446 is applied to leg 1 and leg 2, which switches the hydrophobic/hydrophilic states of the respective gates 444c and 444a. This action closes leg 1 and opens leg 2, as illustrated in the second pane of FIG. 4. At this time, no additional fluid 408 from leg 1 is being wicked toward the detection region 440, but fluid 408 from leg 2 has started wicking into a common leg 424 toward the detection region 440.

As shown in the third pane of FIG. 4, this process is repeated. In particular, the gate 444a in leg 2 is closed and the gate 444b in leg 3 is opened, stopping fluid 408 from leg 2 and allowing fluid 408 from leg 3. This series of actions allows for the correct volume and timing of fluid 408 to move along the wick 404 in order to perform the particular test. Each fluid 408 can be started and stopped repeatedly throughout a measurement if needed. Control electronics, small batteries, and heating elements are sufficiently simple and inexpensive that this could be done in a disposable device or with an inexpensive external controller. In other embodiments, the device 400 can take on different geometric configurations, legs 422 and barriers 444 can be arranged to deliver fluid in different orders to a common leg 424, and there can be more or fewer legs 422 and/or barriers 444.

C. Select Embodiments of Volume-Metering Features

FIGS. 5-8C illustrate various embodiments of volume-metering features configured in accordance with embodiments of the technology. The volume-metering features described below, for example, can be used with the device 100 (FIGS. 1A and 1B) or other suitable capillarity-based devices. The volume-metering features are configured to automatically control or modify a volume of fluid flow along one or more fluid pathways (e.g., pathways 122 of FIGS. 1A and 1B) of a porous wick.

Figure 5:
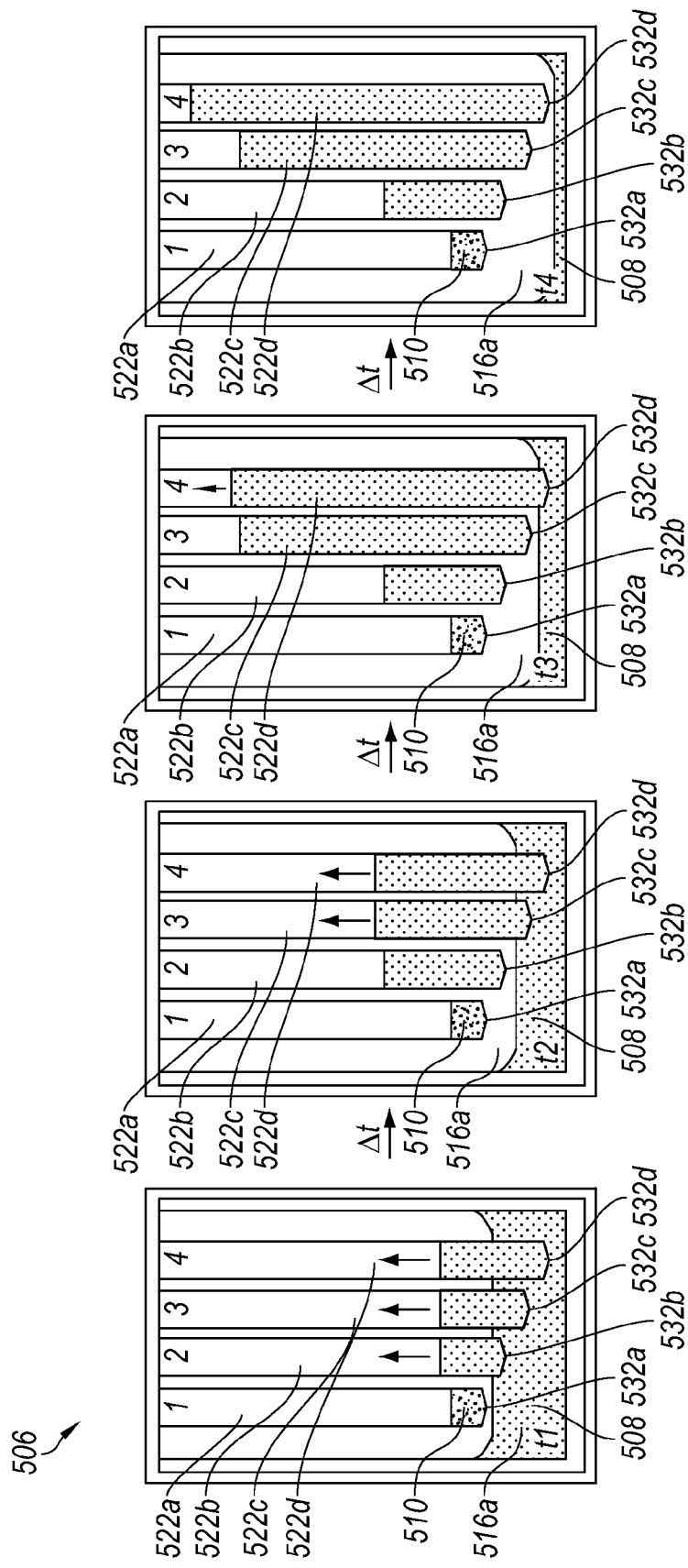
FIG. 5 is a series of time-lapsed front views of a volume-metering element configured in accordance with an embodiment of the technology.
Figure 6:
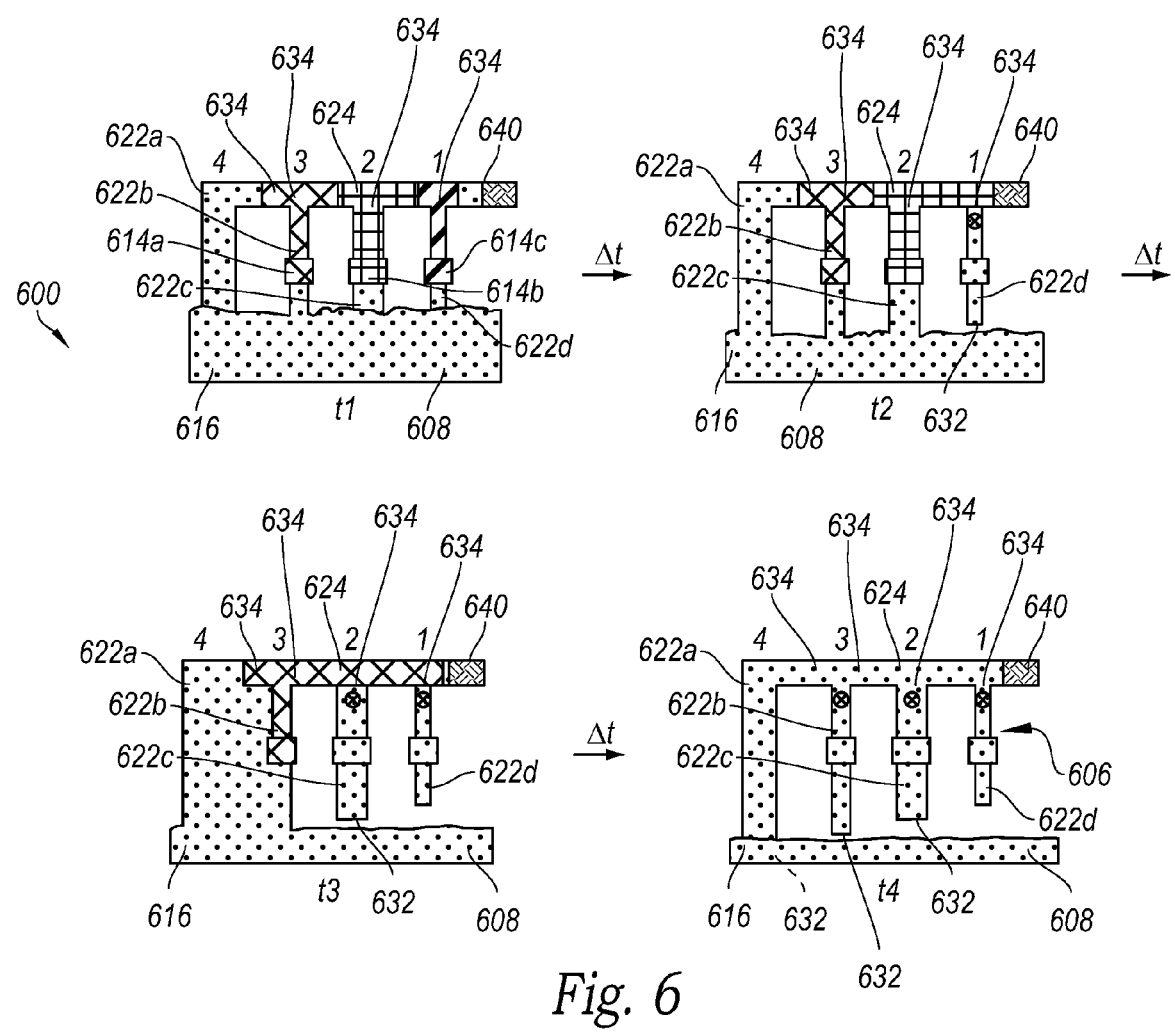
FIG. 6 is a series of time-lapsed front views of a capillarity-based device having a volume-metering element configured in accordance with an embodiment of the technology.

FIGS. 5 and 6 illustrate volume-metering features 506 and 606 that use pathway or leg configuration as an independent control of the shut-off time (and thus volume) of fluid delivered to fluid pathways 522 and 622, respectively. More specifically, the volume-metering features of FIGS. 5 and 6 vary the shut-off time of fluid delivered to a particular pathway by varying the depth that a pathway inlet is submerged into a common fluid well. As fluid from the well wicks into the multiple inlets of the device, the fluid level in the well decreases. When the fluid level falls to a position that is below the bottom of a particular inlet leg, there is no longer a fluidic connection between the well and the input end of the respective pathway, thereby shutting off flow along that particular pathway. This process will occur in sequence for increasing inlet leg lengths.

FIG. 5, for example, is a series of time-lapsed front views of volume-metering feature 506 configured in accordance with an embodiment of the technology. As noted above, the volume-metering feature 506 includes a plurality of pathways 522a-522d (collectively "pathways 522") each configured to be submerged to different depths of the fluid well 516. In other embodiments, there may be more or fewer pathways 522 and not all pathways 522 need have different lengths. When the pathways 522 are first placed proximate to the fluid well 516 at time t1, input ends 532b-532d of legs 2-4 are submerged in fluid 508 in the fluid well 516. The input end 532a of leg 1 is not submerged, and in this embodiment is pre-wetted with a sample 510 to be tested. In other embodiments, more or fewer legs 522 can be pre-wetted.

As the legs 522 begin to wick the fluid 508, the fluid level in the well 516 decreases. Shorter legs 522 will lose access to the fluid source 516 earlier than longer legs, as the fluid 508 leaves the well 516 via wicking along the legs 522b-d. At time t2, for example, the fluid level has dropped below the input end 532b of leg 2, and leg 2 no longer wicks fluid 508 from the well 516. At time t3, leg 3 is no longer in contact with the fluid 508 and has accordingly ceased to wick fluid 508 from the well 516, leaving only leg 4 to continue to wick fluid 508 from the well 516. At time t4, enough fluid 508 has been pulled from the well 516 such that the fluid level in the well 516 no longer reaches the input end 532d of leg 4. Accordingly, at time t4 no legs 532 are contacting fluid 508 in the well 516. In this manner, the shut-off time of each leg 522 is pre-set and controlled.

The shut-off timing of multiple inlet legs 522 can be affected by two parameters in addition to the length of the legs 522 submerged in the well 516: (1) the volumetric uptake rate of all legs 522 that are in fluidic contact with the well 516 and (2) the rate that the fluid level drops. These additional parameters can be manipulated to change the shut-off time(s) of a single leg or multiple legs 522. The volumetric uptake rate can be varied by changing the size, flow velocity, or liquid capacity of the wicking material, or a separate wicking channel can be added that is not connected to the other legs 522. In the latter case, this wick can further be used as a means of creating a humidified environment in regions of the device. The rate that the fluid 508 level drops in the well 516 can also be varied independently of varying the volumetric uptake rate of the legs 522. In one example, the rate that the fluid 508 level drops in the well 516 can be varied by changing the cross sectional area of the well 516 along the plane perpendicular to gravity; for a given volumetric uptake rate, wells 516 with large fluid surface areas drop more slowly than wells with small fluid surface area. In another example, additional components, such as a secondary porous wick that absorbs fluid 508 from the well 516, can alter the rate the fluid 508 drops in the well 516. Further, a change in the material or material properties (i.e., surface treatments) can be used to affect both of these parameters and therefore can be used to control the shut-off timing.

FIG. 6 is a series of time-lapsed front views of a capillarity-based device or analyzer 600 having a volume-metering element 606 configured in accordance with another embodiment of the technology. Specifically, the device 600 uses a volume-metering element 606 where a plurality of pathways 622a-622d (collectively "pathways 622") on a wick 604 have lengths that are designed to "stage" multiple reagents 614a-614c (collectively "reagents 614") in a common leg 624 of the device 600 for sequential delivery to a detection region 640.

Control of the type of reagent 614 that is delivered to the detection region 640 via a particular inlet 622, for example, can be accomplished via spotting of different dried reagents 614 on various legs, either directly on the porous wick 604 or on separate reagent pads (not shown). As fluid 608 from a common well 616 passes onto the input end 632 of a leg 622 having the dried reagent 614, the reagent 614 is reconstituted and flows along the leg 622 and toward an output end 634 into the common leg 624 for sequential delivery to the detection region 640. Reagent delivery can be adjusted such that only one reagent 614 is delivered at a time to the detection region 640 or such that multiple reagents 614 are flowing to the detection region 640 simultaneously in parallel streams, as required by the device application. As in the embodiments discussed above with reference to FIG. 5, inputs 632 of shorter legs 622 stop contacting fluid 608 in the fluid well 616 before inputs 632 of longer legs 622. Accordingly, fluid 608 in shorter legs stops dissolving and delivering reagents 614 before fluid 608 in longer legs 622. Sequential delivery of reagents 614 to the detection region 640 of the device results in the generation of a signal indicating an assay outcome.

In some embodiments, the wick 604 can be composed of a single material in a common fluid well 616. However, in an alternate embodiment, a composite paper network can be composed of multiple materials (with different pore sizes, base material chemistries, and/or surface treatments) for the different inlet legs 622, dry reagent pads 614, main leg 624, detection region 640, etc. These different materials can provide additional flexibility to optimize the dry storage, reconstitution, and delivery of each reagent 614. This can enable more precise control of the integrated sequence of reagent delivery to the detection region 640 of the device. In still further embodiments, the device 600 can include individual wells 616 for each of the inlet legs 622 such that the dimensions and/or fluid level of each well 616 can be varied independently to affect the shut-off timing of the multiple inlet legs 622.

Figure 7A:
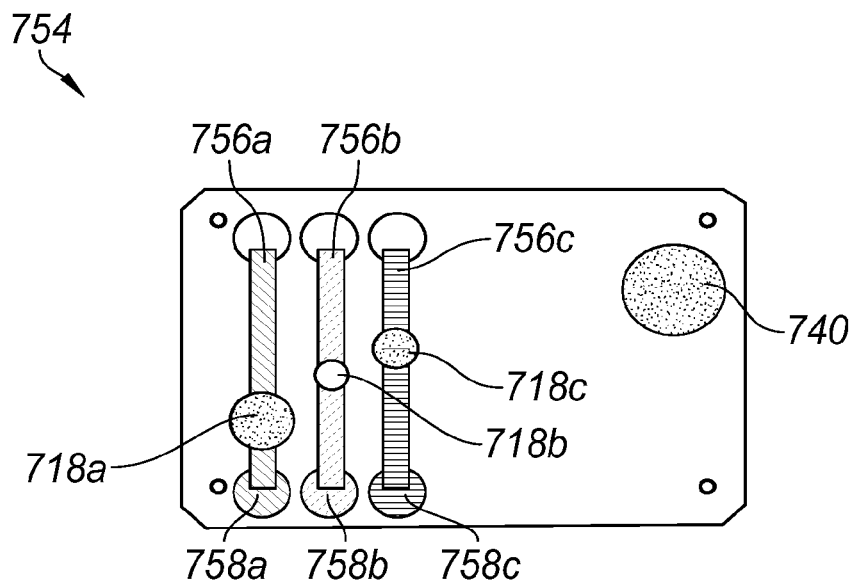
FIG. 7A is a top view of a substrate having volume-metering absorbent pads configured in accordance with an embodiment of the technology.

FIG. 7A is a top view of a substrate 754 having volume-metering absorbent pads 718a-718c (collectively "pads 718") configured in accordance with another embodiment of the technology. Referring first to FIG. 7A, individual absorbent pads 718 are placed on storage wicking strips 756a-756c (collectively "wicking strips 756") that are in fluid contact with reagent storage wells 758. The material and size of the wicking strips 756 are chosen such that they can hold and are capable of delivering a volume of fluid to the metering delivery pad 718 that is in excess of the metering pad 718 fluid capacity.

Fluid reagent from the reagent storage wells 758 is wicked via capillary action successively onto the storage wicking strips 756 and then onto the absorbent pads 718. In one embodiment, the absorbent pads 718 become saturated with reagent from the storage strips 756 in a minute or less. In some embodiments, the pads 718 can be on the same substrate 754 as the fluid wicking strips 756, while in other embodiments the pads 718 can be on a separate substrate. In yet another embodiment, the pads 718 can be attached to the storage strip substrate 754 via adhesive, double-stick foam tape, or other attachment mechanism. In still further embodiments, the absorbent pads 718 are supplied with fluid by means other than wicking fluid from a well 758. For example, in one embodiment, fluid is supplied to the absorbent pads 718 by a syringe or pipette, by one or more pads with an excess of fluid, or by dipping the pads into fluid. Multiple pads 718 can be wetted simultaneously. In the illustrated embodiment, three pads 718 are wetted, but there may be more or fewer pads 718 in other embodiments. The pads 718 can be circular, as illustrated, or can be rectangular, triangular, or other shapes. The fluid volume capacity of the individual pads 718 depends on the dimensional characteristics of the pads 718 and the pad material.

Figure 7B:
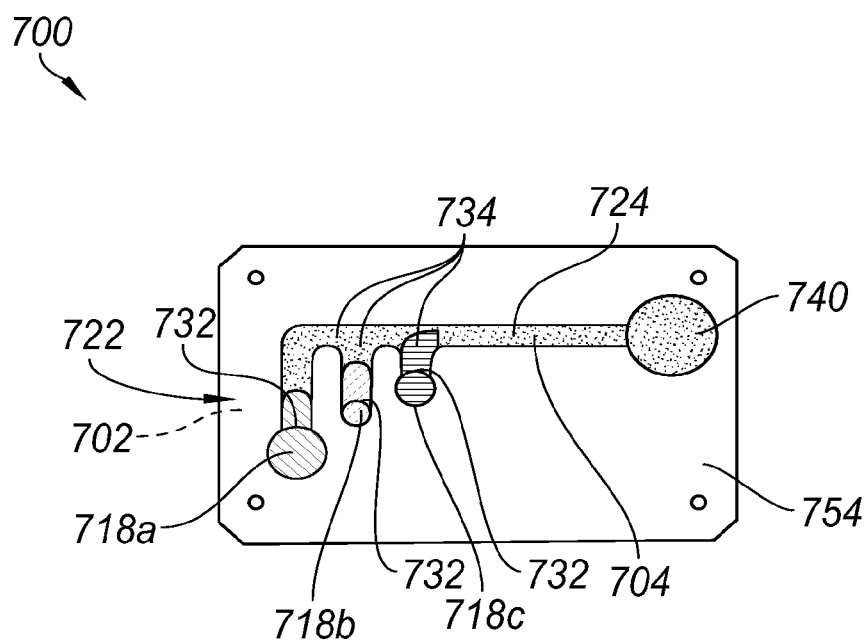
FIG. 7B is a top view of the substrate of FIG. 7A placed on a capillarity-based device configured in accordance with an embodiment of the technology.

FIG. 7B is a top view of the substrate 754 of the capillarity-based device 700 of FIG. 7A. As best seen in FIG. 7B, the substrate 754 can be removably or fixedly placed on the device 700. In several embodiments, the reagent storage wells 758 and the storage wicking strips 756 are not placed on the device 700 with the substrate 754, as the wells 758 and strips 756 are used for loading the pads 718 with fluid and are not needed during a timed assay. The device 700 can have components generally similar to the device 100 described above with reference to FIGS. 1A and 1B. For example, the device 700 can include pathways or legs 722 configured for wicking fluid from an input end 732 to an output end 734 and converging into a common channel 724 and a detection region 740. The substrate 754 can be aligned with the device 700 such that the saturated absorbent pads 718 are adjacent to, and in fluid communication with, input ends 732 of one or more of the pathways 722. In other embodiments, the individual pads 718, rather than the entire substrate 754, are placed on the device 700. In still further embodiments, the pads 718 and device 700 are proximate to one another on a hinged, creased, or otherwise foldable substrate (not shown) and the pads 718 can be contacted with the device 700 by folding the pads 718 onto the device 700. A fixed volume of reagent flows out of the metering delivery pads into the inlets 732 of the pathways 722. The user (not shown) can control the volume delivered to each inlet 732 of the device 700 by varying the size/material of the individual metering delivery pad 718 associated with that inlet 732. Identical porous pads 718 could be loaded with differing volumes of fluid, or porous pads of differing fluid-carrying capacities could be employed. Porous pads can also be designed and selected on the basis of release properties (e.g., material choice or surface treatment), such that time of fluid entering the input legs 722 is limited by the release capacity of the porous pad 718, independent of the pad's fluid-carrying capacity. This is expected to enable independent control of the total volume and total time of reagent delivery to each inlet 732 and allow for fluid flow within the device 700 to be controlled and automatically shut-off.

In an alternate embodiment, instead of loading the absorbent pads 718 with fluid reagents, the metering delivery pads 718 can be pre-loaded with dried reagents so that, with the exception of the sample input, only water or buffer needs to be added to the device 700 to activate the reagents and begin the chemical processing. In another embodiment, additional pads placed downstream on the legs 722 can have dried reagents which are reconstituted upon contacting water or buffer released by the pads 718. This can remove the added complication of adding different reagents to multiple wells 716. Dried reagents can include buffer salts and/or reacting reagents for sample analyte detection.

Figure 8C:
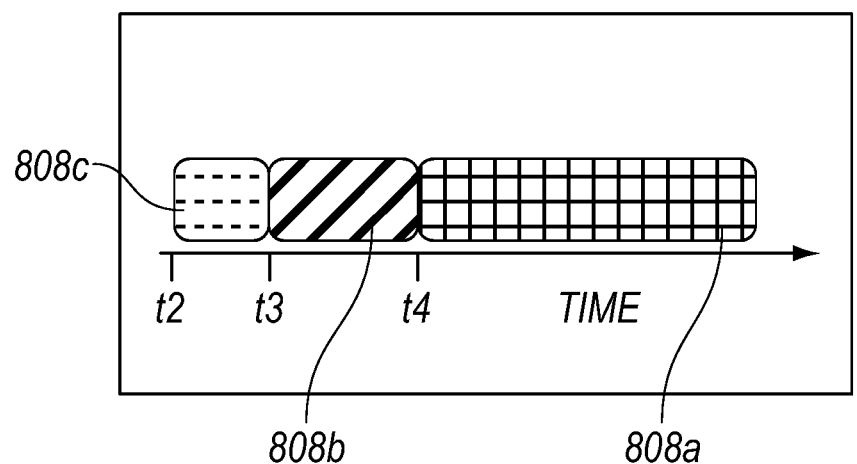
FIG. 8C is a timeline of reagent delivery from the pre-wetted source pads to a wicking pad of the device of FIG. 8A.

FIG. 8A is a series of time-lapsed front views of a capillarity-based device or analyzer 800 configured in accordance with an embodiment of the technology. FIG. 8B is a front view of pre-wetted reagent source pads 818a-818c (collectively "pads 818") for use on the device 800. FIG. 8C is a timeline showing the delivery of reagents from the pre-wetted source pads 818 to a detection region 840. Referring to FIGS. 8A-8C together, the device 800 includes a number of components generally similar to those described above with reference to FIGS. 1A and 1B, including a wick 804 having a plurality of pathways or legs 822a-822c (collectively "pathways 822"). The pathways 822 each include an input end 832 and an output end 834. In the illustrated embodiment, the wick 804 comprises a first substrate. A plurality of pre-wetted pads 818 are on a second substrate 854.

The device 800 allows for sequential reagent delivery to the detection region 840 using a network having three staggered inlets 832 to a common channel 824. While in the illustrated embodiment there are three legs 822 and three pre-wetted pads 818, in other embodiments there can be more or fewer legs 822 and/or pads 818. The device 800 is activated when the second substrate 854 is placed in contact with the wick 804. Specifically, the individual pads 818 are placed in contact with inlets 832 on the individual legs 822. Upon activation, the fluids in the pads are wicked from the input ends 832 toward the detection region 840. Varying volumes of reagent can be introduced into the inlets 832 via the absorbent pads 818. The fluid with the shortest pathway 822c reaches the detection region 840 first and exhausts its fluid source first, while the fluid with the longest pathway 822a takes the longest time to reach the detection region 840 and exhausts its fluid source last. The timing for delivery of multiple fluids (i.e., arrival times and duration of flows) can be varied by changing the path length for fluid travel from each inlet 832 and the volume of fluid applied to each inlet 832. Choice of these parameters, along with the fluid capacity of the materials used will also determine the amount of time the reagent flows can overlap. This can be tailored as needed for the requirements of the specific application.

D. Select Embodiments of Reagent Patterning

Figure 9:
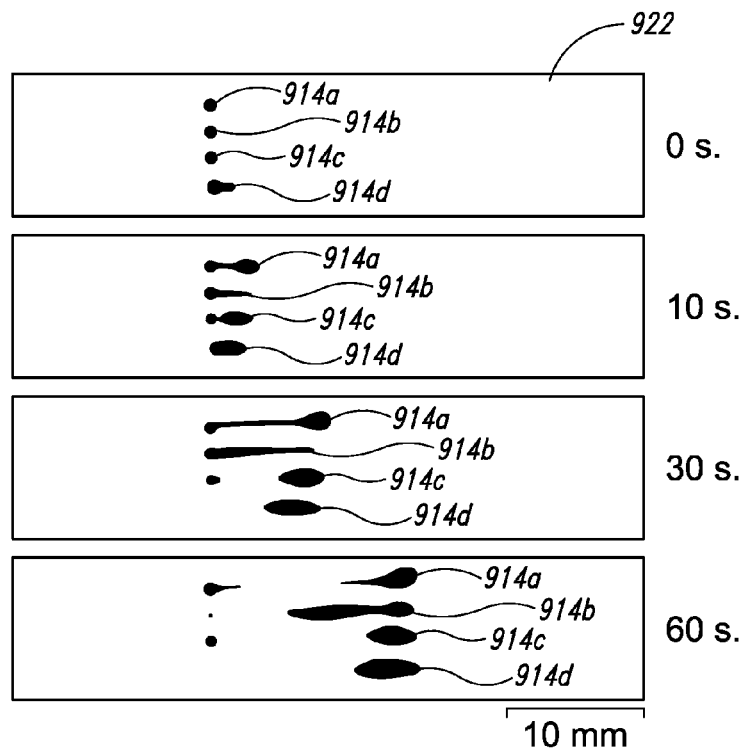
FIG. 9 is a series of time-lapsed front views of a pathway having reagents printed thereon configured in accordance with embodiments of the technology.

FIG. 9 is a series of time-lapsed front views of a pathway 922 having dried reagents 914a, 914b, 914c, 914d (collectively "reagents 914") placed thereon and configured in accordance with embodiments of the technology. In various embodiments, the reagents 914 can be printed, dried, or otherwise disposed on the pathway 922. In the illustrated embodiment, the reagent 914a comprises a first component (e.g., a dried protein-based solution) printed onto the pathway 922. The reagents 914b-914d include various additives that have been combined with the first component prior to printing on the pathway 922. The additives can be selected to achieve a desired temporal or spatial profile of the reagent 914 upon rehydration. For example, the reagent 914b comprises a protein with 1% BSA additive, the reagent 914c comprises a protein with a 5% sucrose and 5% trehalose additive, and the reagent 914d comprises a protein with 5% sucrose, 5% trehalose, and 1% BSA additive. The various combinations produce different rehydration characteristics. For example, without any additives, a significant amount of the printed reagent 914a remains non-specifically bound to the initial printed location, and the portion that does rehydrate into the fluid front leaves a long streak as it flows. The addition of 1% BSA reduces the amount of non-specifically bound reagent 914b, but causes a lag in the rehydration of the bulk. Adding 5% sucrose and 5% trehalose can have the opposite effect—the reagent 914c is dissolved almost immediately into the fluid front, but more remains bound than with the addition of BSA. By adding all three components, a combination characteristics is observed; very little reagent 914d remains non-specifically bound, while the bulk of the rehydration occurs immediately at the wetting front.

Selection of a particular additive can be made to achieve a desired temporal or spatial profile. The additives can comprise various materials, such as a sugar or a non-specific protein. By including sugar as an additive, for example, the viscosity of the rehydrated reagent solution is increased. This increase in viscosity can be used to provide control over the dissolution time of reagents dried in storage cavities in polydimethylsiloxane (PDMS) devices. In addition to imparting control over the dissolution of dried reagents 914, sugars such as sucrose and trehalose can be used to stabilize dried proteins. The hydroxyl groups of the sugar molecules substitute for the waters of hydration of the protein which are lost upon drying, and can act to preserve the protein's native conformation. Further, the high glass transition temperature of trehalose (106° C.) ensures that at elevated temperatures trehalose remains in the glassy state with lower molecular mobility, and can thus protect the protein against degradation and crystallization.

Figures 10A, 10B:
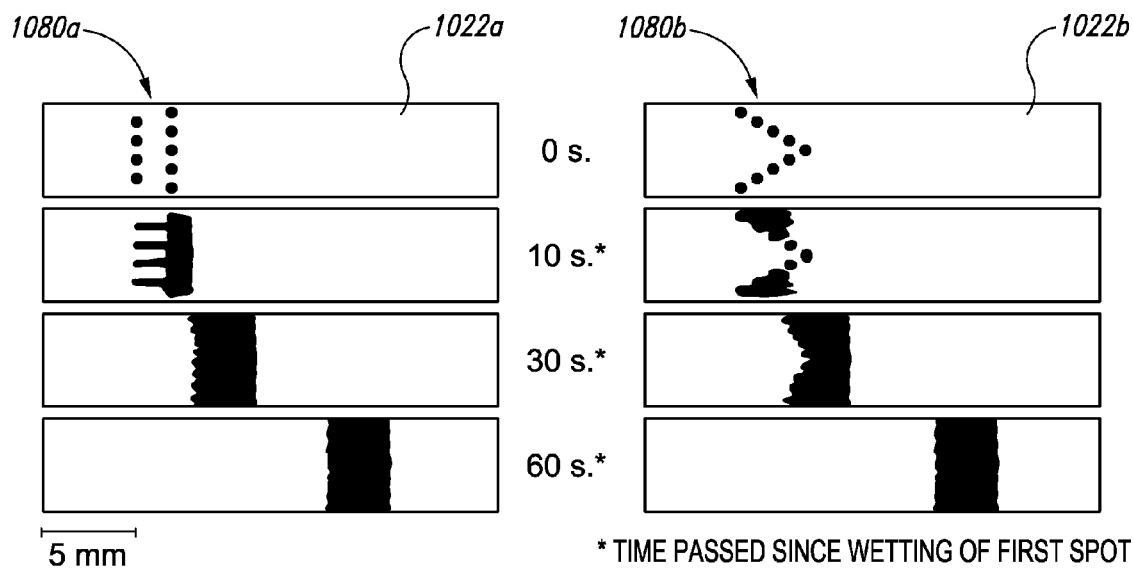
FIGS. 10A and 10B are series of time-lapsed front views of a pathway having reagents printed in reagent patterns configured in accordance with embodiments of the technology.

FIGS. 10A and 10B are series of time-lapsed front views of pathways 1022a, 1022b having reagents printed in a reagent pattern 1080a, 1080b (collectively "reagent pattern 1080") configured in accordance with embodiments of the technology. FIG. 10A illustrates a linear, spotted reagent pattern 1080a while FIG. 10B illustrates a V-shaped reagent pattern 1080b. Referring to FIGS. 10A and 10B together, the reagent printing patterns 1080 can achieve spatially-controlled reagent pulses upon rehydration.

The reagent patterns 1080 comprise spatially uniform individual spots of reagent, patterned perpendicular to a direction of flow. Pulses such as these can be used in devices to ensure consistency of reagent delivery to downstream locations such as a capture zone. As the fluid front reaches these reagent patterns 1080, the reagent is dissolved with the liquid to yield a consistent, near-uniform pulse to a downstream region. By varying the amount of reagent printed in each spot and the number of spots arrayed across the strip, the amount of reagent delivered by the pulse can be tuned to suit the needs of a particular assay. In some embodiments, the initial pattern of reagent spots does not affect the resulting pulse: all spots can rehydrate into the wetting front, and diffuse together as long as the y-separation of spots is small (e.g., 0.5 mm). This distance between spots, as well as the amount of reagent printed within each storage spot can affect the uniformity of the resultant pulse.

FIG. 11A is a schematic illustration of a capillarity-based device 1100 having a series of reagents 1114a, 1114b, and 1114c (collectively "reagents 1114") printed thereon in accordance with embodiments of the technology. The reagents 1114 are printed on separate regions of a porous wick 1104. Similar to the wick 104 described above with reference to FIG. 1, the porous wick 1104 includes a plurality of pathways 1122a, 1122b, 1122c. The arrangement of reagents 1114 patterned on various regions of the wick 1104 provides for a controlled combination of reagents 1114 for particular microfluidic assays. For example, printing reagents 1114 separately and later combining them via rehydration can facilitate the storage of reagents that must not interact until they are mixed immediately before use. The particular assay illustrated can utilize the technique of storing gold-enhancement reagents separately and then combining them immediately prior to use in order to test for the Malaria antigen *P. falciparum* Histidine-rich protein 2 (PfHRP2).

The reagents 1114a, 1114b, and 1114c are spotted in sequential regions along a pathway 1122. In further embodiments, one or more of the reagents 1114 can be printed on a separate or common pathway. In a particular embodiment, the reagents 1114 (an enhancer 1114a, activator 1114b, and initiator 1114c) are printed in series on the first pathway 1122, while an antibody 1150 is printed on the third pathway 1122c. The reagents 1114 are combined in series upon rehydration, thus not mixing prior to the initiation of the assay. The reagents 1114 or antibody 1150 can comprise any type of reagent or antibody such as a labeled antibody (e.g., gold, HRP), an enzymatic substrate (e.g., DAB, TMB), trehalose, sucrose, silver enhancement reagents, or other components.

Figure 12A:
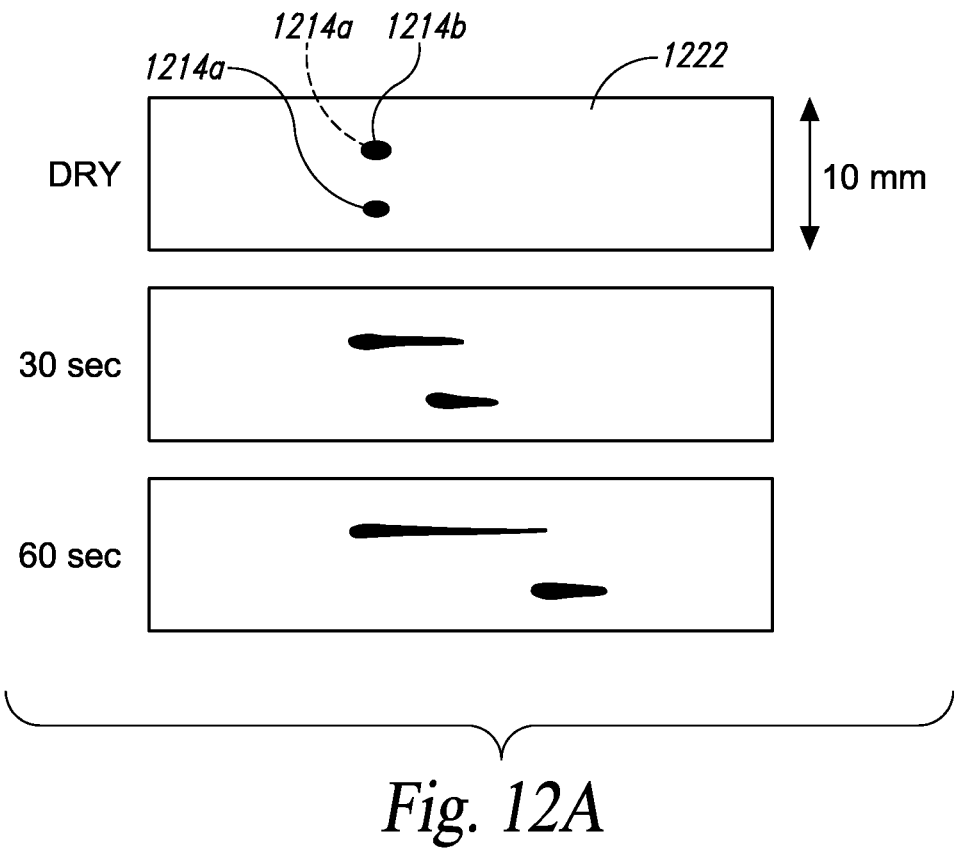
FIG. 12A is a series of time-lapsed front views of a pathway having reagents printed thereon configured in accordance with embodiments of the technology.

FIG. 11B is a series of time-lapsed front views of the capillarity-based device 1100 of FIG. 11A during reagent 1114 rehydration in accordance with embodiments of the technology. As described above, the enhancer 1114a, activator 1114b, and initiator 1114c lose functionality if they are dried for storage after they have been mixed. Thus, they must be stored dry in separate regions and recombined on device for delivery to downstream regions of the assay. The gold enhancement reagents 1114 printed separately can be combined upon rehydration to yield a bolus of complete gold enhancement solution, which is then capable of enhancing the gold signal generated in a PfHRP2 detection assay. The first frame illustrates the assay at initial time t=0. After 15 minutes, the second frame illustrates a visible signal from the antibody 1150 in a detection region 1140. After 60 minutes, the third frame illustrates a fully-developed signal. In further embodiments, the device 1100 can be used for other tests. For example, these methods can be applied to enzymatic signal generation such as HRP-TMB or HRP-DAB FIG. 12A is a series of time-lapsed front views of a pathway 1222 having reagents 1214 printed thereon and configured in accordance with embodiments of the technology. In the illustrated embodiment, a second reagent 1214b (e.g., sucrose) is printed on top of a first reagent 1214a (e.g., a protein) to alter the duration of the first reagent's hydration. In the illustrated embodiment, the first reagent 1214a having the second reagent 1214b overprinted thereon is compared to a control spot (only the first reagent 1214a). In the illustrated embodiment, the over-patterning of the second reagent 1214b extends the duration of the first reagent's 1214a hydration as compared to the control. In further embodiments, over-patterning can shorten or otherwise alter the underlying reagent's 1214a hydration. In still further embodiments, the first reagent 1214a and second reagent 1214b are in an alternate layered or side-by-by configuration.

Figure 12B:
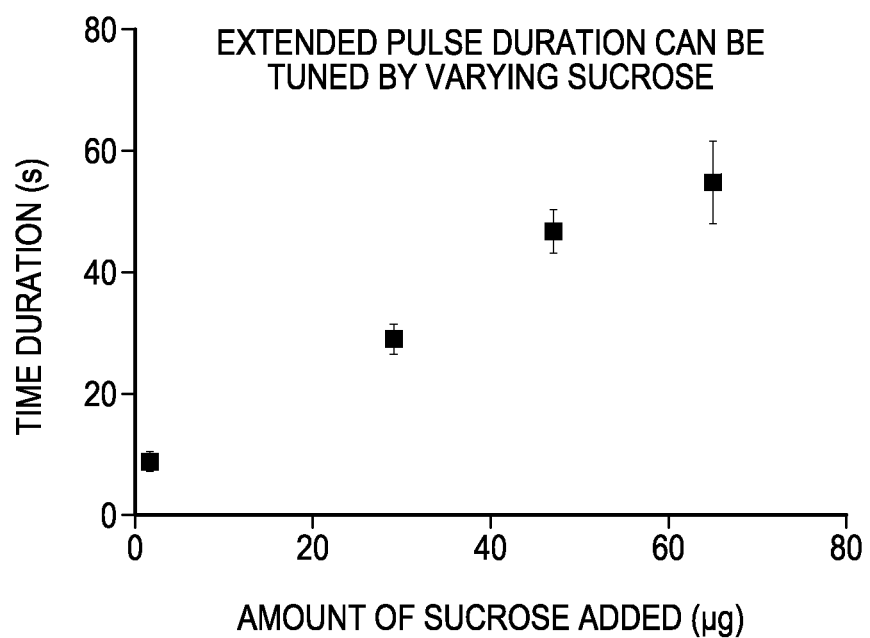
FIG. 12B is a plot illustrating a relationship between reagent pattern and pulse duration in accordance with embodiments of the present technology.

FIG. 12B is a plot illustrating a relationship between reagent pattern and reagent pulse duration in accordance with embodiments of the present technology. In some embodiments, an increased amount of the second reagent 1214b (e.g., sucrose) over-patterned on the first reagent 1214a, extends the duration of the first reagent's rehydration compared to a control. In further embodiments, an increased amount of an over-patterned second reagent 1214b shortens or otherwise alters the duration of rehydration.

Figure 13A:
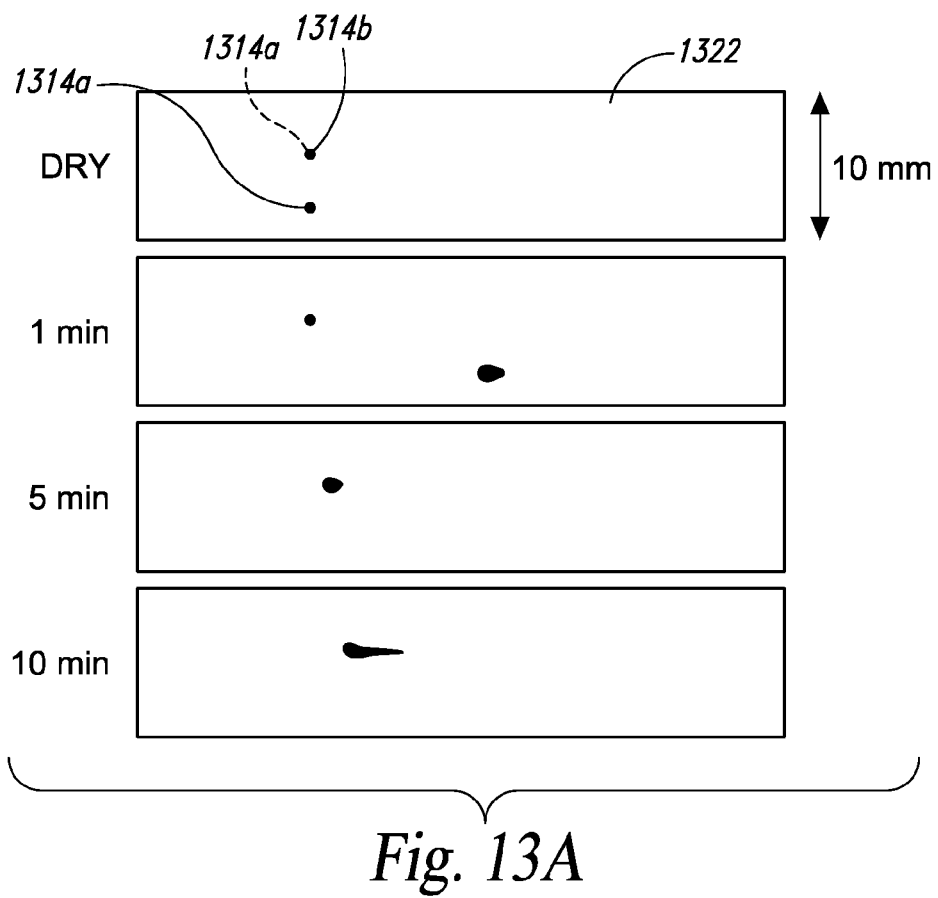
FIG. 13A is a series of time-lapsed front views of a pathway having reagents printed thereon configured in accordance with embodiments of the technology.

FIG. 13A is a series of time-lapsed front views of a pathway 1322 having reagents 1314a, 1314b printed thereon in accordance with embodiments of the technology. In the illustrated embodiment, the spatial or temporal rehydration profile of the first reagent 1314a is manipulated by adding a ring of the second reagent 1314b around the first reagent 1314a. As compared to a control sample having only the first reagent 1314a, the addition of the second reagent 1314b ring barrier delays rehydration of the first reagent 1314a. Dramatically different delays (e.g., from a few seconds to several minutes or more) can be achieved by printing secondary reagent 1314b barriers containing different consistencies (e.g., different amounts of sucrose). In various embodiments, the secondary reagent 1314b barrier can comprise multiple secondary reagents 1314b and/or can have different shapes or patterns relative to the first reagent 1314a (e.g., a circular or hexagonal ring or portion of a ring, or a linear barrier). In further embodiments, the secondary reagent 1314b barrier can speed-up the rehydration temporal profile or delay it by larger or smaller amounts than described above. In still further embodiments, the secondary reagent 1314a can alter the spatial rehydration profile of the first reagent 1314a (e.g., by fanning out or streamlining the rehydration path of the first reagent 1314a).

Figure 13B:
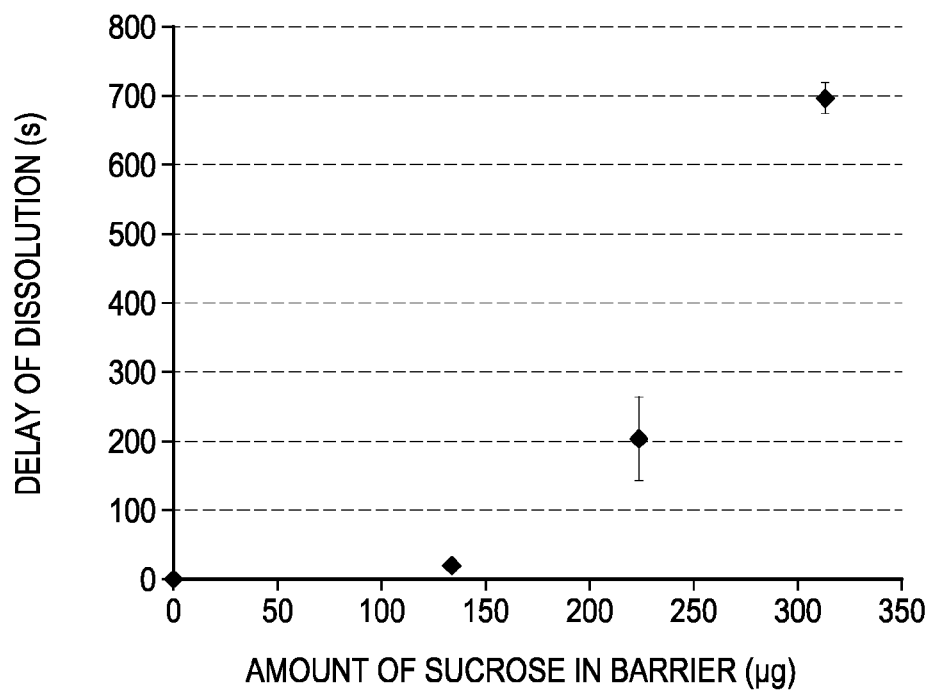
FIG. 13B is a plot illustrating a relationship between reagent pattern and delayed reagent dissolution in accordance with embodiments of the present technology.

FIG. 13B is a graph illustrating a relationship between reagent pattern and delayed reagent dissolution in accordance with embodiments of the present technology. As illustrated, varying the makeup of the secondary reagent 1314b can alter the temporal effect of the barrier, with more secondary reagent 1314b (e.g., sucrose) causing an increased delay in first reagent 1314a dissolution.

Examples

1. A device for performing chemical processes, the device comprising:
    a porous wick comprising a pathway defined by an input end, an output end, and a length between the input end and the output end, and a pathway width, wherein the pathway is configured to wick fluid from the input end to the output end by capillary action; and
    a reagent placed on the pathway, wherein the reagent is placed in a pattern configured to control a spatial or temporal distribution of the reagent along the pathway upon flow of fluid along the pathway.

2. The device of example 1 wherein the reagent placed on the pathway comprises a first reagent placed on a first portion of the pathway, and wherein the device further comprises a second reagent placed on a second portion of the pathway spaced apart from the first portion.

3. The device of example 1 wherein the reagent placed on the pathway comprises a first reagent, and wherein the device further comprises a second reagent placed on top of the first reagent.

4. The device of example 1 wherein the reagent placed on the pathway comprises a first reagent, and wherein the device further comprises a second reagent placed on the pathway and at least partially surrounding the first reagent.

5. The device of example 1 wherein the reagent placed on the pathway comprises a first reagent placed on a first pathway, and wherein the device further comprises a second pathway and a second reagent placed on the second pathway.

6. The device of example 1 wherein the reagent comprises at least one of a gold enhancement reagent, a labeled antibody, an enzymatic substrate, a silver enhancement reagent, a nucleic acid amplification reagent, trehalose, or sucrose.

7. The device of example 1, further comprising at least one of a volume-metering element or a flow-metering element, wherein the volume-metering element or flow metering element is integral to the porous wick and is positioned to modify a rate or volume of fluid flow along the porous wick.

8. The device of example 7 wherein the flow-metering element comprises a soluble barrier along the porous wick.

9. The device of example 7 wherein the flow-metering element comprises a switchable barrier along the porous wick.

10. The device of example 7 wherein the volume-metering element or a flow-metering element comprises a geometric characteristic of the pathway.

11. The device of example 1 wherein the pathway comprises a first pathway, and wherein the porous wick further comprises a second pathway in fluid communication with the first pathway, and wherein the second pathway has a second length defined by a second input end and a second output end, and wherein the second pathway has a second length less than the length of the first pathway.

12. The device of example 1 wherein the reagent is placed in an array pattern configured to generate a near-uniform reagent distribution across the width of the pathway upon wetting of the pathway.

13. The device of example 1 wherein the pathway comprises a first pathway, and wherein the device further comprises:
    a second pathway defined by a second input end, a second output end, and a second length between the second input end and the second output end; and
    an intersection where the first pathway and the second pathway meet and form a common pathway, wherein the common pathway comprises a receiving region, an extraction region, an amplification region, and a detection region.

14. A method for performing chemical processes, the method comprising:
    wicking a volume of a fluid along a pathway of a porous matrix from an input end of the pathway, through a reagent printed on the pathway in a reagent pattern, and toward an output end of the pathway; and
    controlling a spatial or temporal distribution profile of the reagent.

15. The method of example 14 wherein the reagent comprises a first reagent, and wherein controlling a spatial or temporal distribution profile of the first reagent comprises:
   wicking the volume of a fluid through a secondary reagent printed on top of the first reagent; and
   extending a duration of the first reagent's rehydration.

16. The method of example 14 wherein the reagent comprises a first reagent, and wherein controlling a spatial or temporal distribution profile of the reagent comprises wicking the volume of a fluid through the first reagent and then through a second reagent printed on the pathway and spaced apart from the first reagent.

17. The method of example 14 wherein the reagent comprises a first reagent, and wherein controlling a spatial or temporal distribution profile of the first reagent comprises:
   wicking the volume of a fluid through a secondary reagent printed around the first reagent; and
   delaying an initiation of the first reagent's rehydration.

18. The method of example 14 wherein controlling a spatial or temporal distribution profile of the reagent comprises generating a pre-defined reagent pulse.

19. The method of example 14 wherein the chemical processes comprises at least one of an immunoassay or a nucleic acid amplification test.

20. The method of example 14 wherein the reagent comprises a dried reagent and wherein the porous matrix comprises nitrocellulose.

21. A method for manufacturing a capillarity-based analyzer, the method comprising:
   forming a first leg having an input end, an output end, and a width, wherein the first leg is configured to wick a first fluid from the input end toward the output end;
   forming a second leg having an input end, an output end, and a width, wherein the second leg is configured to wick a second fluid from the input end toward the output end, and wherein the second leg converges with the first leg at an intersection point; and
   printing a reagent pattern on the first leg, wherein the reagent pattern is configured to modify a temporal or spatial aspect of fluid delivery to the intersection region.

22. The method of example 21 wherein printing a reagent pattern on the first leg comprises printing a first reagent on a first portion of the first leg and printing a second reagent on a second portion of the first leg spaced apart from the first portion.

23. The method of example 21 wherein printing a reagent pattern on the first leg comprises printing a plurality of reagent deposits across the width of the first leg.

24. The method of example 21 wherein printing a reagent pattern on the first leg comprises printing a sucrose barrier around a dried reagent.

25. The method of example 21 wherein printing a reagent pattern on the first leg comprises printing a first reagent on the first leg and printing a second reagent on top of the first reagent.

26. The method of example 21 wherein printing a reagent pattern on the first leg comprises printing a solution comprising a first component and a second component on the first leg.

27. The method of example 21 wherein printing a reagent pattern on the first leg comprises printing a reagent pattern on nitrocellulose.

28. The method of example 21, further comprising forming a flow-metering element or a volume-metering element on at least one of the first leg or the second leg.

The capillarity-based devices and analyzers disclosed herein offer several advantages over conventional systems. By allowing a user to control temporal and spatial aspects of reagent delivery within the diagnostic device, increased assay accuracy and sensitivity can be achieved. Further, the use of spaced-apart reagent patterning keeps reagents separate until rehydration. The devices disclosed herein are expected to improve assay functionality while maintaining a manufacturing cost equal to that of conventional rapid diagnostic tests (RDTs). This new approach to point-of-care diagnostics combines the sophistication of chemical processing developed in microfluidics with the simplicity and low cost of lateral flow immunoassays.

From the foregoing it will be appreciated that, although specific embodiments of the technology have been described herein for purposes of illustration, various modifications may be made without deviating from the spirit and scope of the technology. For example, the presence/configuration of the base or housing, the number of pathways, number of reagents, type of reagents, spotting pattern of reagents, the use of pre-wetted pads, the specific types of fluids, and material choices for various components of the devices described above with reference to FIGS. 1A-13B may vary in different embodiments of the technology. While particular embodiments are described with reference to reagent printing, in further embodiments reagents may be placed on a wick or substrate by other means, such as drying reagents onto the substrate or placing a source pad or other reagent-containing material on the substrate, etc. Further, certain aspects of the new technology described in the context of particular embodiments may be combined or eliminated in other embodiments. For example, in the embodiments illustrated above, various combinations of reagent patterning or features may be combined into a single device. Moreover, while advantages associated with certain embodiments of the technology have been described in the context of those embodiments, other embodiments may also exhibit such advantages, and not all embodiments need necessarily exhibit such advantages to fall within the scope of the technology. Accordingly, the disclosure and associated technology can encompass other embodiments not expressly shown or described herein. Thus, the disclosure is not limited except as by the appended claims.

We claim:

1. A device for performing chemical processes, the device comprising:
   a porous wick comprising a pathway defined by an input end, an output end, a length between the input end and the output end, and a pathway width, wherein the pathway is configured to wick fluid from the input end to the output end by capillary action;
   a first reagent placed on the pathway, wherein the reagent is placed in a pattern configured to control a spatial or temporal distribution of the first reagent along the pathway upon flow of fluid along the pathway; and
   a second reagent placed in a ring around the first reagent on the pathway.

2. The device of claim 1 wherein the first reagent is placed on a first portion of the pathway, and the second reagent is placed on a second portion of the pathway spaced apart from the first portion.

3. The device of claim 1 wherein the pathway is a first pathway, and the device further comprises a second pathway and a third reagent placed on the second pathway.

4. The device of claim 1 wherein the first reagent comprises at least one of a gold enhancement reagent, a labeled antibody, an enzymatic substrate, a silver enhancement reagent, a nucleic acid amplification reagent, trehalose, or sucrose.

5. The device of claim 1, further comprising at least one of a volume-metering element or a flow-metering element, wherein the volume-metering element or flow metering element is integral to the porous wick and is positioned to modify a rate or volume of fluid flow along the porous wick.

6. The device of claim 5 wherein the flow-metering element comprises a soluble barrier along the porous wick.

7. The device of claim 5 wherein the flow-metering element comprises a switchable barrier along the porous wick.

8. The device of claim 5 wherein the volume-metering element or the flow-metering element comprises a geometric characteristic of the pathway.

9. The device of claim 1 wherein the pathway comprises a first pathway, and wherein the porous wick further comprises a second pathway in fluid communication with the first pathway, and wherein the second pathway has a second length defined by a second input end and a second output end, and wherein the second pathway has a second length less than the length of the first pathway.

10. The device of claim 1 wherein the first reagent is placed in an array pattern configured to generate a near-uniform reagent distribution across the width of the pathway upon wetting of the pathway.

11. The device of claim 1 wherein the pathway comprises a first pathway, and wherein the device further comprises:
    a second pathway defined by a second input end, a second output end, and a second length between the second input end and the second output end; and
    an intersection where the first pathway and the second pathway meet and form a common pathway, wherein the common pathway comprises a receiving region, an extraction region, an amplification region, and a detection region.

12. The device of claim 1 wherein the second reagent is configured to delay the temporal distribution of the first reagent along the pathway and/or fan out the spatial distribution of the first reagent along the pathway.

13. The device of claim 1 wherein the second reagent is configured to speed up the temporal distribution of the first reagent along the pathway and/or streamline the spatial distribution of the first reagent along the pathway.

14. The device of claim 1 further comprising a third reagent placed in a ring about the first reagent on the pathway.

* * * * *